US012702276B2

(12) United States Patent
Finocchi et al.

(10) Patent No.: US 12,702,276 B2
(45) Date of Patent: Aug. 11, 2026

(54) HOLDER FACILITY FOR HOLDING A MEDICAL INSTRUMENT

(71) Applicant: Siemens Healthineers Endovascular Robotics, Inc., Newton, MA (US)

(72) Inventors: Rodolfo Finocchi, Boston, MA (US); Ankur Kapoor, Plainsboro, NJ (US); Erin Girard, Madison, CT (US); Young-Ho Kim, West Windsor, NJ (US); Tommaso Mansi, Plainsboro, NJ (US)

(73) Assignee: Siemens Healthineers Endovascular Robotics, Inc., Newton, MA (US)

( * ) Notice: Subject to any disclaimer, the term of this patent is extended or adjusted under 35 U.S.C. 154(b) by 61 days.

(21) Appl. No.: 18/987,356

(22) Filed: Dec. 19, 2024

(65) Prior Publication Data

US 2025/0113979 A1 Apr. 10, 2025

Related U.S. Application Data

(63) Continuation of application No. 17/033,297, filed on Sep. 25, 2020, now abandoned.

(30) Foreign Application Priority Data

Sep. 27, 2019 (DE) ..................... 10 2019 214 868.9

(51) Int. Cl.
*A61B 1/00* (2006.01)
*A61B 34/30* (2016.01)
*A61B 90/57* (2016.01)

(52) U.S. Cl.
CPC ...... *A61B 1/00147* (2013.01); *A61B 1/00149* (2013.01); *A61B 34/30* (2016.02); *A61B 90/57* (2016.02); *A61B 2034/301* (2016.02)

(58) Field of Classification Search
CPC . A61B 1/00147; A61B 1/00149; A61B 34/30; A61B 90/57; A61B 2034/301
(Continued)

(56) References Cited

U.S. PATENT DOCUMENTS 5,375,588 A * 12/1994 Yoon .................. A61B 17/3462 606/1
5,480,410 A 1/1996 Cuschieri
(Continued)

FOREIGN PATENT DOCUMENTS

| KR | 101957344 | 3/2019 |
|---|---|---|
| WO | 9507056 | 3/1995 |

(Continued)

OTHER PUBLICATIONS

European Search Report Rec'd for Corresponding EP Application No. 20198286.5, mailed Feb. 5, 2021, with English Machine Translation.

(Continued)

*Primary Examiner* — Anita M King

(57) ABSTRACT

A holder facility for holding a medical instrument includes a first receiving element, a second receiving element, and at least three diaphragm elements. The at least three diaphragm elements within a diaphragm layer are arranged between the first and second receiving elements about a common rotation axis. The first and second receiving elements each have an opening for receiving the medical instrument. The first and second receiving elements are movable around about the common rotation axis relative to one another. Each of the at least three diaphragm elements is forcibly moved by mechanical coupling. For a movement of the first receiving element relative to the second receiving element about the common rotation axis, there is a forcibly-guided movement of the at least three diaphragm elements such that the at least three diaphragm elements hold a medical instrument
(Continued)

arranged in the opening of the first and second receiving elements.

20 Claims, 12 Drawing Sheets

(58) Field of Classification Search
USPC .............................................................. 606/1
See application file for complete search history.

(56) References Cited

U.S. PATENT DOCUMENTS

| | | | | |
|---|---|---|---|---|
| 6,589,167 | B1 | 7/2003 | Shimomura | |
| 7,766,894 | B2 | 8/2010 | Weitzner et al. | |
| 7,922,656 | B2 * | 4/2011 | Beckman | A61B 90/08 600/204 |
| 8,480,618 | B2 | 7/2013 | Wenderow et al. | |
| 11,116,592 | B2 | 9/2021 | Xu | |
| 11,246,672 | B2 * | 2/2022 | Landey | A61B 34/20 |
| 11,642,159 | B2 | 5/2023 | Kincaid | |
| 12,239,402 | B2 * | 3/2025 | Waterbury | A61B 46/10 |
| 2004/0215063 | A1 * | 10/2004 | Bonadio | A61B 17/3462 128/897 |
| 2008/0249371 | A1 | 10/2008 | Beckman et al. | |
| 2014/0371627 | A1 | 12/2014 | Leimbach | |
| 2015/0164596 | A1 | 6/2015 | Romo et al. | |
| 2018/0252359 | A1 | 9/2018 | Janway et al. | |
| 2019/0192242 | A1 | 6/2019 | Xu | |
| 2020/0060646 | A1 | 2/2020 | Lindenroth | |
| 2020/0061339 | A1 | 2/2020 | Lindenroth et al. | |
| 2022/0125465 | A1 | 4/2022 | Beckman | |

FOREIGN PATENT DOCUMENTS

| | | |
|---|---|---|
| WO | 9524864 | 9/1995 |
| WO | 2012087668 | 6/2012 |

OTHER PUBLICATIONS

Loschak, Paul M., et al. "A 4-DOF robot for positioning ultrasound imaging catheters." ASME 2015 International Design Engineering Technical Conferences and Computers and Information in Engineering Conference. American Society of Mechanical Engineers, 2015. pp. 1-10.

Stereotaxis, "Stereotaxis V-Drive Robotic Navigation System", Available: http://www.stereotaxis.com/products/vdrive/, Stand: Jan. 14, 2019.

* cited by examiner 1, 2
13
14
11
12

1, 2
12
33
11
14

HOLDER FACILITY FOR HOLDING A MEDICAL INSTRUMENT

This application is a continuation of U.S. patent application Ser. No. 17/033,297, filed Sep. 25, 2020, which claims the benefit of German Patent Application No. DE 10 2019 214 868.9, filed on Sep. 27, 2019, which is hereby incorporated by reference in its entirety.

BACKGROUND

The present embodiments relate to a holder facility for holding a medical instrument.

For the precise examination of an object to be examined (e.g., for vascular diseases and/or tumor diseases, as well as for interventions, such as for vasodilation and/or for placement of an angioplasty in the object being examined), elongated and/or flexible medical instruments are frequently used. In such cases, the object being examined may be a human and/or animal patient, for example. The medical instrument is further frequently embodied as a surgical instrument (e.g., as a catheter and/or guide wire, and/or as a diagnostic instrument, such as an endoscope with an ultrasound head for a transesophageal echocardiogram (TEE probe), and/or a bronchoscope). While the high mechanical flexibility and/or deformability of the medical instruments frequently represents an important basis for use in an intervention and/or examination, precise guidance of the instrument may be rendered more difficult by the attributes.

Guidance facilities for guiding a catheter are known from the prior art, where at least sections of the catheter are moved translationally within the guidance facility by a number of drive wheels. The guidance facility in this case is frequently only configured for a predetermined medical instrument. An extent of the translational movement of the medical instrument by the guidance facility is further frequently restricted to a few centimeters.

In addition, the document Loschak et al., “A 4-DOF Robot for Positioning Ultrasound Imaging Catheters”, in *Proc ASME Des Eng Tech Conf.* 2015, 5A:V05AT08A046, discloses a robotic guidance facility for guiding a catheter. In this facility (e.g., through friction between the guidance facility and the catheter), this may disadvantageously result in a torsion and/or deformation of the catheter. This may render a precise guidance of the catheter as a medical instrument significantly more difficult.

Further, robot-assisted facilities for guidance of endoscopes are known, where the endoscopes are frequently to be embodied specifically for the robot-assisted facility. The known robot-assisted facilities further frequently require a large amount of space, which may be a disadvantage, precisely in a clinical (e.g., surgical) environment.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a facility for holding a medical instrument securely and flexibly is provided.

According to a variant, a holder facility includes a first receiving element, a second receiving element, and at least three diaphragm elements. In this variant, the at least three diaphragm elements are arranged within a diaphragm layer between the first receiving element and the second receiving element about a common axis of rotation of the first receiving element and the second receiving element. In this variant, the common axis of rotation essentially runs at right angles to the diaphragm layer. The first receiving element and the second receiving element each further have an opening for receiving the medical instrument (e.g., at least on the common axis of rotation). In addition, the first receiving element and the second receiving element are able to be moved around relative to one another about the common axis of rotation. Further, the at least three diaphragm elements each include at least one first coupling element. In this case, the first receiving element and/or the second receiving element includes at least one second coupling element for each of the at least three diaphragm elements. Each of the at least three diaphragm elements within the diaphragm layer in which these are arranged are further forcibly guided by mechanical coupling between the respective at least one first coupling element of the diaphragm element and the at least one second coupling element. In addition, when the first receiving element is moved relative to the second receiving element about the common axis of rotation, there is a forcibly-guided movement of the at least three diaphragm elements within the diaphragm layer by the first receiving element and the second receiving element towards the opening for receiving the medical instrument such that the at least three diaphragm elements hold a medical instrument arranged in the opening of the first receiving element and the second receiving element.

In this case, the medical instrument may include a surgical instrument (e.g., a catheter and/or a guide wire, and/or a diagnostic instrument, such as an endoscope with an ultrasound head for a transesophageal echocardiogram (TEE probe), and/or a bronchoscope and/or a laparoscope). For example, the medical instrument may be elongated and/or mechanically deformable.

The first receiving element and/or the second receiving element may be embodied in the shape of a disk. In this case, the first receiving element and/or the second receiving element may have a central plane. In this case, a spatial extent of the first receiving element and/or the second receiving element along the respective central plane may be greater compared to a spatial extent of the first receiving element and/or the second receiving element at right angles to the respective central plane. The first receiving element and/or the second receiving element may have an edge. The edge may also have a raised area. Through this, it may be made possible for the first receiving element and/or the second receiving element to enclose the respective other receiving element at least in part.

The first receiving element and/or the second receiving element may at least in part have a mechanically stable (e.g., non-deformable) shape. Further, the common axis of rotation of the first receiving element and/or the second receiving element may form an axis of symmetry of the first receiving element and/or the second receiving element in each case.

Each of the at least three diaphragm elements may have two contact surfaces in each case for arrangement (e.g., direct arrangement) on a contact surface of at least two neighboring diaphragm elements in each case. This makes it possible for there to be a mobility of the at least three diaphragm elements while simultaneously preserving the stability. In this variant, the at least two contact surfaces of each of the at least three diaphragm elements may have a low-friction surface.

In addition, the diaphragm layer may include an area (e.g., a disk-shaped are) of space between the first receiving element and the second receiving element. The diaphragm layer may be formed, for example, by the spatial extent of the at least three diaphragm elements between the first receiving element and the second receiving element. In this case, the at least three diaphragm elements within the diaphragm layer may be arranged between the first receiving element and the second receiving element about the common axis of rotation (e.g., in the form of a ring). For example, the at least three diaphragm elements may be arranged along a common circle about the common axis of rotation within the diaphragm layer.

The first receiving element and/or the second receiving element (e.g., a raised area on the edge of the first receiving element and/or the second receiving element) may at least partly enclose the diaphragm layer. This enables a protection (e.g., a seal) against any external mechanical and/or chemical effect on the at least three diaphragm elements to be provided.

In one embodiment, the common axis of rotation of the first receiving element and the second receiving element runs essentially at right angles (e.g., not parallel) to the diaphragm layer.

The opening for receiving the medical instrument is embodied such that the medical instrument is able to be introduced completely and with free movement in at least one spatial direction into the opening. In this case, a maximum diameter of the medical instrument that is able to be introduced into the opening of the first receiving element and the second receiving element is delimited by a spatial extent of the opening of the first receiving element and the second receiving element.

In one embodiment, the first receiving element and the second receiving element are able to be moved relative to one another about the common axis of rotation. In this case, the first receiving element and/or the second receiving element may be able to be moved about the common axis of rotation. The first receiving element and the second receiving element are further able to be moved rotationally relative to one another. In addition, the first receiving element and/or the second receiving element may be able to be taken out of the arrangement and/or introduced into the arrangement.

In one embodiment, the at least three diaphragm elements may have two first coupling elements. The first receiving element and the second receiving element may, for example, each have a second coupling element for each of the at least three diaphragm elements. This enables each of the at least three diaphragm elements to be coupled mechanically to the first receiving element and the second receiving element using the two second coupling elements in each case. In this case, one of the two second coupling elements in each case for each of the at least three diaphragm elements may further be embodied for positioning.

In one embodiment, by moving the first receiving element relative to the second receiving element about the common axis of rotation, there may be a change in the arrangement of the second coupling elements of the first receiving element and/or the second receiving element in relation to the arrangement of the at least three diaphragm elements. Provided the first receiving element and the second receiving element for each of the at least three diaphragm elements each have a second coupling element, the movement of the first receiving element relative to the second receiving element enables there to be a change in the arrangements of the second coupling elements of the first receiving element and the second receiving element in relation to one another. Through the mechanical coupling between the first coupling elements of the at least three diaphragm elements and the second coupling elements, a forcibly-guided movement of the diaphragm elements within the diaphragm layer may be made possible through this.

In one embodiment, the second coupling elements of the first receiving element and/or the second receiving element are embodied such that the at least three diaphragm elements are able to be moved in a forcibly-guided manner towards the opening for receiving the medical instrument (e.g., rotated and/or displaced). At least one of the second coupling elements of the first receiving element and/or the second receiving element may further be embodied in a circular shape and/or curved and/or as a straight line.

In one embodiment, the at least three diaphragm elements may be held movably by the mechanical coupling between the at least one first coupling element and the respective at least one second coupling element within the diaphragm layer (e.g., within a predetermined radius of the common axis of rotation).

In such cases, all medical instruments that are able to be introduced into the opening of the first receiving element and the second receiving element are held by the at least three diaphragm elements. When the first receiving element is moved relative to the second receiving element about the common axis of rotation, an end point of the movement may be predetermined by a mechanical resistance when the at least three diaphragm elements strike the medical instrument arranged in the opening of the first receiving element and the second receiving element. In one embodiment, the medical instrument may be held by the at least three diaphragm elements after a movement of the first receiving element relative to the second receiving element about the common axis of rotation up to the end point of the movement. A movement of the first receiving element relative to the second receiving element in a first direction of movement in such a way that the at least three diaphragm elements are forcibly guided towards the opening may be referred to as closing the holder facility. In a similar way to this, a movement of the first receiving element relative to the second receiving element in a second direction of movement in such a way that the at least three diaphragm elements make a forcibly guided movement away from the opening may be referred to as opening the holder facility.

In this case, the holding of the medical instrument by the at least three diaphragm elements may be made possible by a mechanical coupling between the medical instrument and the at least three diaphragm elements. In one embodiment, the medical instrument may be held in position by the at least three diaphragm elements in relation to the holder facility (e.g., in a non-displaceable and/or rotationally-stable manner). In this case, the at least three diaphragm elements for holding the medical instrument may each exert a pressure on the medical instrument.

In a further form of embodiment of the holder facility, the at least one first coupling element of the respective diaphragm element may be embodied as an elongated guide, in which at least one second coupling element of the first receiving element and/or of the second receiving element is accommodated in each case. In this case, the at least one second coupling element of the first receiving element and/or the second receiving element in each case may be embodied such that the at least one second coupling element is able to be received into an elongated guide of the respective diaphragm element. This enables a mechanical coupling between the at least one second coupling element of the first receiving element and/or the second receiving element in each case and the elongated guide of the respective diaphragm element to be made possible. In one embodiment, the respective diaphragm element is able to be moved (e.g., displaced) along a guide path within the elongated guide. One axis of rotation in each case for each of the at least three diaphragm elements may further be able to be predetermined by receiving the at least one second coupling element within the elongated guide of the respective diaphragm element. In this case, each of the at least three diaphragm elements within the diaphragm layer may be rotatable about the predetermined axis of rotation. Further, at least one of the first coupling elements of the respective diaphragm element may be embodied to surround the accommodated second coupling element at least partly (e.g., completely).

In a further embodiment of the holder facility, the at least one second coupling element of the first receiving element and/or the second receiving element may be embodied as an elongated guide, in which the respective at least one first coupling element of the respective diaphragm element is accommodated. In this embodiment, the at least one first coupling element of each of the at least three diaphragm elements may be embodied in such a way that the at least one first coupling element is able to be received into an elongated guide of the first receiving element and/or the second receiving element in each case. This enables a mechanical coupling between the at least one first coupling element of the diaphragm element in each case and the elongated guide to be made possible. In one embodiment, the at least one first coupling element of the diaphragm element is able to be moved (e.g., displaced) along a guide path within the elongated guide of the first receiving element and/or the second receiving element. One axis of rotation in each case for each of the at least three diaphragm elements may further be able to be predetermined by accommodating the at least one second coupling element within the longitudinal guide. In this embodiment, each of the at least three diaphragm elements within the diaphragm layer may be able to be rotated about the predetermined axis of rotation. Further, at least one of the second coupling elements of the first receiving element and/or the second receiving element may be embodied to surround the received first coupling element at least partly (e.g., completely).

In a further form of embodiment of the holder facility, the at least three diaphragm elements may be arranged at least partly overlapping one another within the diaphragm layer. Through this, a space-saving arrangement of the at least three diaphragm elements within the diaphragm layer may be made possible. Further, through the at least partly overlapping arrangement of the at least three diaphragm elements, the mechanical coupling between the medical instrument and the at least three diaphragm elements (e.g., in a longitudinal direction of the medical instrument) may be improved. In addition, a greater stability of the arrangement of the at least three diaphragm elements within the diaphragm layer in relation to a force effect exerted by the medical instrument being held may be made possible with an at least partly overlapping arrangement of the at least three diaphragm elements.

In a further form of embodiment of the holder facility, the at least one first coupling element of the respective diaphragm element in each case and/or the at least one second coupling element of the first and/or the second receiving element in each case may be embodied as a raised area and/or a cutout of the respective diaphragm element. In this embodiment, the at least one first coupling element may be embodied as a pin-shaped and/or hemispherical-shaped and/or cylindrical raised area of the respective diaphragm element. The at least one second coupling element may further be embodied as a pin-shaped and/or hemispherical-shaped and/or cylindrical raised area of the first and/or the second receiving element.

The at least one first coupling element may further be embodied as a cylindrical and/or hemispherical-shaped cutout of the respective diaphragm element. In addition, the at least one second coupling element may be embodied as a cylindrical and/or hemispherical-shaped cutout of the first receiving element and/or the second receiving element.

Further, the at least one first coupling element may be embodied as a raised area and/or cutout of the respective diaphragm element in such a way that a, for example, external shape of the respective diaphragm element is formed by the at least one first coupling element. For example, the at least one first coupling element may be embodied as a raised area and/or cutout on a side surface and/or edge and/or corner of the diaphragm element in each case. Further, the at least one second coupling element may be embodied as a raised area and/or cutout of the first receiving element and/or the second receiving element in such a way that a shape of the first receiving element and/or the second receiving element is formed by the at least one second coupling element. For example, the at least one second coupling element may be embodied as a raised area and/or cutout on a side surface and/or edge and/or corner of the first receiving element and/or the second receiving element. Provided the first receiving element and/or the second receiving element has an edge and/or a raised area, the respective at least one second coupling element may be arranged on the edge and/or the raised area. This enables a contact surface between the at least one first coupling element of the respective diaphragm element and the corresponding at least one second coupling element of the first receiving element and/or the second receiving element for mutual mechanical coupling to be maximized.

In a further form of embodiment of the holder facility, the at least three diaphragm elements may feature a softer material by comparison with the first receiving element and/or the second receiving element. In this embodiment, each of the at least three diaphragm elements may include at least one grip surface that touches the medical instrument when the holder facility is closed. The grip surface may feature a non-slip material and/or an adhesive material. Through this, a secure holding of the medical instrument by the at least three diaphragm elements may be made possible.

The at least three diaphragm elements may further consist, at least partly, of a softer material by comparison with the first receiving element and/or the second receiving element (e.g., visco foam and/or rubber). This enables it to be made possible for the at least three diaphragm elements to cling to the medical instrument in the closed state of the holder facility. Through this, a maximization of the grip surface between the at least three diaphragm elements and the medical instrument may be achieved. This further makes it possible for the at least three diaphragm elements to adapt especially well to a shape (e.g., an irregular shape) of a medical instrument. This enables flexible use of the holder facility for many medical instruments of different shapes to be made possible.

In a further form of embodiment of the holder facility, the at least three diaphragm elements may be arranged in the same shape about the common axis of rotation. This enables an even holding of the medical instrument by the at least three diaphragm elements to be made possible. A tilting of the at least three diaphragm elements for the forcibly-guided movement within the diaphragm layer may be prevented by an even arrangement about the common axis of rotation. In addition, with an even arrangement of the at least three diaphragm elements about the common axis of rotation, it may be achieved that the medical instrument is held centered on the common axis of rotation (e.g., centered in relation to the at least three diaphragm elements).

In a further form of embodiment of the proposed holder facility, the at least three diaphragm elements along the diaphragm layer may have a triangular and/or circle segment-shaped form. This enables an arrangement of the at least three diaphragm elements next to one another (e.g., without mutual overlapping) within the diaphragm layer to be made possible. Through a triangular and/or circle segment-shaped form of the at least three diaphragm elements along the diaphragm layer, a mutual guidance of the diaphragm elements for a movement within the diaphragm layer is further made possible. In this embodiment, neighboring diaphragm elements may slide along on each other in each case.

In a further form of embodiment of the holder facility, the opening for receiving the medical instrument of the first receiving element and/or the second receiving element may be embodied as a hole and/or slot. When the opening for receiving the medical instrument is embodied as a hole, the medical instrument may be able to be introduced at least along the common axis of rotation. One end of the medical instrument may be introduced into the opening, where the medical instrument is able to be moved at least up to a prespecified position within the opening.

When the opening for receiving the medical instrument is embodied as a slot, the holder facility may be able to be put onto the medical instrument. The medical instrument may further be able to be introduced from the side through the slot into the holder facility. This enables it to be made possible for the holder facility to be fitted to the medical instrument even when all ends of the medical instrument are fastened.

Through a movement of the first receiving element relative to the second receiving element about the common axis of rotation, an arrangement of the two openings embodied as a slot may further be changed such that a medical instrument arranged in the opening cannot be taken out of the holder facility from the side. Through this, an especially secure accommodation of the medical instrument within the opening of the first and the second receiving element may be made possible.

In a further form of embodiment of the holder facility, the first receiving element and/or the second receiving element may be embodied in the shape of a wheel. In this case, the first receiving element and/or the second receiving element may be embodied round and disk-shaped along the respective central plane (e.g., about the common axis of rotation). In one embodiment, the first receiving element and/or the second receiving element are able to be moved rotationally in relation to one another about the common axis of rotation. With a wheel-shaped design of the first receiving element and/or the second receiving element, a simple rotational movement of the first receiving element relative to the second receiving element about the common axis of rotation may be made possible. A wheel-shaped embodiment of the first receiving element and/or the second receiving element may be space-saving.

In a further form of embodiment of the holder facility, the first receiving element and/or the second receiving element may be embodied as a toothed wheel and/or pulley wheel. Through this, a driven movement of the first receiving element and/or the second receiving element may be made possible. In this form of embodiment, an embodiment as a toothed wheel refers to an arrangement of tooth-shaped (e.g., triangular, raised areas around a circumference of the wheel-shaped first receiving element and/or second receiving element). The first receiving element and/or the second receiving element may further have a cutout around the circumference, where a belt to drive the movement of the first receiving element and/or the second receiving element may be placed within the cutout. An embodiment of the first receiving element and/or the second receiving element as a toothed wheel and/or pulley wheel makes possible an improved mechanical coupling (e.g., through friction) to a drive element.

In a further form of embodiment of the holder facility, the holder facility may also include a motorized drive element that is configured to move the first receiving element relative to the second receiving element about the common axis of rotation. In this embodiment, the motorized drive element may include a motor (e.g., an electric motor). The motorized drive element may further include a transmission element that couples the motor mechanically to the first receiving element and/or the second receiving element. In this case, the transmission element may be embodied, for example, as a belt and/or toothed wheel and/or transmission. In one embodiment, through the motorized drive element for moving the first receiving element relative to the second receiving element, a precise and/or remotely-controlled movement may be made possible. For example, the holder facility for holding the medical instrument may be opened or closed by the motorized drive element especially easily and/or repeatedly.

In a further form of embodiment of the holder facility, the holder facility may also include a fixing element that is embodied to lock the first receiving element in place in relation to the second receiving element. The medical instrument is only held firmly by the at least three diaphragm elements for as long as the first receiving element and the second receiving element in the closed state of the holder facility remain at rest relative to one another. A fixing element, which is embodied to lock the first receiving element in relation to the second receiving element (e.g., in a fixed position), may therefore be advantageous for securely holding the medical instrument. For example, the first receiving element may be locked in place in relation to the second receiving element by the fixing element in the closed state of the holder facility.

In this embodiment, the fixing element may be embodied, for example, as a lock (e.g., a lever and/or a plug connection between the first receiving element and the second receiving element) and/or as part of the motorized drive element. In addition, the fixing element may have at least one magnet. The fixing element may further be able to be plugged into the first receiving element and/or the second receiving element and/or be able to be introduced into the first receiving element and/or in the second receiving element. This enables the first receiving element and the second receiving element to be connected (e.g., reversibly) mechanically rigidly, where a movement of the first receiving element in relation to the second receiving element may be prevented by the fixing element. The first fixing element may further be locked in relation to the second receiving element as a function of an alignment and/or orientation.

The locking of the first receiving element in relation to the second receiving element may further be able to be released by the fixing element. For example, it may be made possible to open the holder facility by releasing the locking of the first receiving element in relation to the second receiving element.

In a further form of embodiment of the holder facility, the holder facility may also include a diaphragm fixing element that is embodied to lock the at least three diaphragm elements. In this embodiment, the diaphragm fixing element may be arranged within the diaphragm layer and/or around the diaphragm layer. In one embodiment, at least one of the diaphragm elements may be locked in a fixed position by the diaphragm fixing element. For example, with an arrangement of the at least three diaphragm elements without mutual overlapping within the diaphragm layer, a locking of an individual diaphragm elements may be sufficient for locking all diaphragm elements. This may be made possible, for example, by mutual friction of the diaphragm elements on one another. The diaphragm fixing element may further be embodied to mechanically couple the at least one first coupling element of at least one diaphragm element rigidly (e.g., immovably) to the corresponding at least one second coupling element of the first receiving element and/or the second receiving element.

The diaphragm fixing element may further be embodied to lock in place the arrangement of the at least three diaphragm elements (e.g., in the closed state of the holder facility). In this case, the diaphragm fixing element may be embodied, for example, as a circumferential band and/or ring and/or lever and/or clamp. In one embodiment, the holder facility may be opened by releasing the lock of the at least three diaphragm elements. With an arrangement of the diaphragm fixing element within the diaphragm layer, a space-saving design may be made possible.

In one embodiment, through a locking of the at least three diaphragm elements by the diaphragm fixing element, a movement of the first receiving element and/or the second receiving element may be made possible. For example, the first receiving element and/or the second receiving element may be able to be removed after closure of the holder facility and locking of the at least three diaphragm elements by the diaphragm fixing element. This may enable the first receiving element and/or the second receiving element to be able to be used in a further holder facility.

In one embodiment, the diaphragm fixing element and/or one of the at least three diaphragm elements may include a fastening element for fastening to a medical device and/or to a patient support facility. This enables the medical instrument to be held by the holder facility on the medical device and/or the patient support facility.

In a further form of embodiment of the holder facility, the first receiving element for each of the at least three diaphragm elements may include a second coupling element in each case. The second coupling element is cut out as an elongated guide that is embodied as a cutout and runs in a straight line. The second receiving element may further include a further second coupling element for each of the at least three diaphragm elements in each case. The further second coupling element is cut out as an elongated guide and runs in a curve. In this case, the first receiving element and the second receiving element may be embodied in a wheel shape. In addition, the first receiving element and/or the second receiving element may be embodied as a toothed wheel. In this case, the opening for receiving the medical instrument of the first receiving element and the second receiving element may be embodied as a slot and may be delimited by the common axis of rotation. The at least three diaphragm elements may further have a triangular shape. In this embodiment, each of the at least three diaphragm elements may have two first coupling elements in each case. The two first coupling elements are embodied as pin-like raised areas. Further, a first of the two first coupling elements of each of the at least three diaphragm elements may be arranged on a side of the diaphragm element facing towards the first receiving element in each case. In this case, a second of the two first coupling elements of each at least three diaphragm elements may be arranged on a side of the diaphragm element facing towards the second receiving element. The two first coupling elements of each of the at least three diaphragm elements may further not lie on a spatial axis parallel to the common axis of rotation.

Through this, a space-saving design of the holder facility may be made possible.

In a further aspect, the present embodiments relate to a movement facility for moving a medical instrument including a holder facility, a transmission element, and a connection element. In this case, the holder facility may be embodied to hold the medical instrument. The transmission element may further transmit a movement between at least one part of the holder facility and the connection element (e.g., bidirectionally). In addition, the connection element may be arranged at a distance from the holder facility.

In this case, the holder facility may, for example, be a holder facility as described above. The transmission element may further have a belt and/or a toothed wheel and/or a transmission. Through this, a precise and direct transmission of a movement between at least one part of the holder facility and the connection element may be made possible. In one embodiment, a movement may be transmitted between the first receiving element and/or the second receiving element and/or the at least three diaphragm elements of the holder facility and the connection element (e.g., bidirectionally). Further, a movement of the holder facility as a whole (e.g., in a closed state with the medical instrument arranged therein) may be able to be transmitted between the holder facility and the connection element by the transmission element. In this facility, the movement may include rotational movement of the holder facility (e.g., of the medical instrument). The arrangement of the connection element at a distance from the holder facility enables a suitable arrangement of the connection element (e.g., at a distance from the medical instrument) to be made possible.

In addition, the connection element may be embodied as a sleeve and/or shaft and/or an interface (e.g., an electronic interface). The connection element and/or the transmission element may further have at least one movement sensor that is embodied to detect a movement of the connection element and/or a movement of at least a part of the holder facility. In this case, the movement sensor may include an optical and/or electromagnetic and/or ultrasound-based movement sensor, for example. Through this, an electronic (e.g., bidirectional) transmission of the movement between the at least one part of the holder facility (e.g., the first receiving element and/or the second receiving element and/or the at least three diaphragm elements) and the connection element is made possible.

The holder facility may further have another movement sensor that is embodied to detect a movement of the medical instrument relative to the holder facility (e.g., relative to the at least three diaphragm elements). In this case, the other movement sensor may include an optical and/or electromagnetic and/or ultrasound-based movement sensor, for example. Provided the medical instrument has a marker structure and/or at least one marker object, the other movement sensor may detect the movement of the medical instrument based on the movement of the marker structure and/or the at least one marker object.

In a further form of embodiment of the movement facility, the transmission element may have a belt drive and/or a toothed wheel drive. In this embodiment, the belt drive may have at least one belt and/or a pulley wheel, where the belt transmits a movement between the at least one part of the holder facility and the pulley wheel. The toothed wheel drive may further have at least one toothed wheel, where the toothed wheel may be coupled mechanically to the at least one part of the holder facility. The connection element may be coupled mechanically and/or electronically to the pulley wheel and/or the toothed wheel. Through this, a precise and direct transmission of the movement between the at least one part of the holder facility and the connection element may be made possible.

In a further form of embodiment of the movement facility, the holder facility may have a number of degrees of freedom of movement. In this embodiment, the transmission element may transmit the movement between the holder facility and the connection element in accordance with the number of degrees of freedom of movement (e.g., bidirectionally and/or simultaneously). For example, the first receiving element and/or the second receiving element and/or the at least three diaphragm elements may each have at least one degree of freedom of movement. For example, the first receiving element and/or the second receiving element may have a degree of freedom of movement for rotation about the common axis of rotation. The at least three diaphragm elements may further each have a degree of freedom of movement within the forcibly-guided movement between the opening and closing of the holder facility.

In one embodiment, the transmission element includes a number of transmission channels (e.g., belts and/or toothed wheels and/or lines) that are embodied to transmit a degree of freedom of movement of the holder facility between the holder facility and the connection element in each case. In one embodiment, the number of degrees of freedom of movement of the holder facility may be transmitted in parallel and/or simultaneously and/or independently of one another and/or bidirectionally by the transmission element. Through this, an individual and/or simultaneous activation of the number of degrees of freedom of movement of the holder facility may be made possible by the connection element. A detection of a movement of at least one part of the holder facility corresponding to a degree of freedom of movement in each case may further be detected (e.g., separately) by the connection element. In this case, the connection element and/or the transmission element may each include a movement sensor for detection of a degree of freedom of movement of the holder facility in each case.

In a further form of embodiment of the movement facility, the connection element may have a connection receptacle for each of the degrees of freedom of movement of the holder facility in each case. In this embodiment, the connection receptacles may be embodied as a sleeve and/or shaft and/or an interface (e.g., an electronic interface). In one embodiment, at least one of the connection receptacles may be embodied for mechanical and/or electronic coupling of a robot and/or of a medical device and/or of a processing unit.

In a further form of embodiment of the movement facility, the movement facility may also include a housing. In this embodiment, the housing may enclose the holder facility and the transmission element at least partly such that the medical instrument is able to be introduced into the holder facility. In one embodiment, the holder facility and the transmission element may be protected by the housing against any external mechanical and/or chemical influence. Hygienic cleaning of the movement facility may also be facilitated by the housing. In addition, a mechanical stability of the arrangement including the holder facility, the transmission element, and the connection element may be improved by the housing. In one embodiment, the housing may be embodied as a sterile barrier between the holder facility with the transmission element and the connection element. For example, the holder facility with the connection element may be coupled through the housing (e.g., the sterile barrier) mechanically and/or electromagnetically to the connection element.

In a further form of embodiment of the movement facility, the movement facility may also include a fastening element. In this embodiment, the fastening element may be embodied for fastening the movement facility to a medical device and/or to a patient support facility. The fastening element may further include a stand and/or a screw clamp and/or a clamp mounting and/or a robot arm. In one embodiment, the movement facility may be fastened (e.g., movably) by the fastening element to a medical device (e.g., an intervention robot and/or a robot arm and/or a medical imaging device, and/or a patient support facility). Through this, a movement of the medical instrument arranged in the movement facility relative to the movement facility (e.g., to the fastening element) may be made possible. The movement facility may further be fastened movably by the fastening element (e.g., to a guide rail) of the medical device and/or the patient support facility.

In a further form of embodiment of the movement facility, the fastening element may have a motor drive that is embodied to move the movement facility. In this embodiment, the motor drive may include an electric motor, for example. The motor drive may further be embodied, for example, as a roller drive for moving the movement facility along a guide rail. Through this, a precise and guided movement of the movement facility (e.g., of the medical instrument) along a fastening on the medical device and/or the patient support facility may be made possible.

In a further form of embodiment of the movement facility, the movement facility may also include a motor element. In this embodiment, the motor element may be embodied to be linked (e.g., mechanically) to the connection element such that the motor element and the connection element are movement-coupled. The motor element may, for example, include a motor (e.g., an electric motor). The motor element may further be coupled electronically and/or mechanically to the connection element. Through this, a movement is able to be transmitted between the motor element and at least one part of the holder facility by the transmission element. A sterile barrier may further be arranged between the motor element and the holder facility with the transmission element. In this embodiment, the housing may at least partly enclose the holder facility and the transmission element and thus form a sterile barrier from the motor element and/or the fastening element.

In this embodiment, the motor element may be embodied both for opening and/or closing the holder facility, and also for movement of the holder facility as a whole. Through this, a rotational movement of the medical instrument held in the holder facility may be made possible.

In a further form of embodiment of the movement facility, the motor element may include a sensor element for detection of a movement of at least one part of the holder facility. In this case, the sensor element may include an optical and/or electromagnetic sensor, for example. A control of the movement of the at least one part of the holder facility by the motor element may take place as a function of the detected movement of the at least one part of the holder facility and/or of another part of the holder facility. For example, a rotational movement of the holder facility as a whole may take place as a function of whether the holder facility is in the closed state and/or the opened state.

Through the forms of embodiment of the movement facility described above, support for medical personnel (e.g., a doctor) in placement and/or guidance and/or movement of the medical instrument (e.g., within the framework of an intervention) may be made possible.

Described below is a method for moving a medical instrument using a first movement facility. The advantages of the method essentially correspond to the advantages of the movement facility for moving a medical instrument described by way of example above. Features, advantages, or alternate forms of embodiment may likewise also be transferred to the other claimed subject matter and vice versa.

In a further aspect, the present embodiments relate to a method for moving a medical instrument by a first movement facility (e.g., a first movement device). In this aspect, in act r1), the medical instrument may be arranged in the first movement facility. For example, the medical instrument may be introduced into the opening of the first receiving element and the second receiving element of the holder facility of the first movement facility.

Further, in act r2), a first position of at least a section of the medical instrument is determined. In this case, for example, a marking and/or a marker object on the medical instrument may be used to determine the first position. The first position may be determined relative to a reference point in space and/or to a fastening element of the movement facility and/or relative to an object being examined and/or relative to a medical imaging device. The first position may further be determined as a reference position of the medical instrument after the closure of the holder facility.

In addition, in act r3), the first receiving element and/or the second receiving element of the holder facility of the first movement facility may be moved such that the at least three diaphragm elements hold the medical instrument. In this case, the holder facility may be closed. In one embodiment, the medical instrument, after act r3), may be held stably and firmly by the at least three diaphragm elements of the holder facility.

Further, in act r4), the first movement facility may be moved from an initial position into a target position. In this case, the first movement facility may, for example, be rotated and/or displaced in its entirety. The holder facility of the first movement facility may further be rotated (e.g., relative to the first movement facility). In this case, the medical instrument may be moved as well, at least in sections. This is made possible, for example, by the firm and stable hold on the medical instrument in the holder facility.

In act r5), a further position of the at least one section of the medical instrument may be determined. In this case, for example, an angle of rotation and/or a distance covered and/or a number of rotations may be determined as the further position (e.g., in reaction to the first position and/or to the reference position).

Hereafter, in act r6), the first receiving element and/or the second receiving element of the holder facility of the first movement facility may be moved such that the medical instrument is released by the at least three diaphragm elements. In this case, the holder facility is opened, and the medical instrument is released.

In this method, the acts r2) to r6) may be repeated (e.g., iteratively) until a target position of the at least one section of the medical instrument is reached. Through this, a forward movement (e.g., translational movement) and/or a rotational movement of the medical instrument (e.g., over a great distance) may be made possible, where the movement facility is moved repeatedly over a comparatively small distance.

In a further aspect, the present embodiments relate to a coordination facility for coordinated movement of a medical instrument. In this aspect, the coordination facility may include a first movement facility and at least one further movement facility. The first movement facility and the at least one further movement facility may further be arranged at a distance from one another. In this case, the first movement facility and the at least one further movement facility may be embodied to move the same medical instrument. The first movement facility and the at least one further movement facility may further move the medical instrument in a coordinated manner.

In this case, the first movement facility and/or the at least one further movement facility may, for example, be a movement facility described above. The first movement facility and the at least one further movement facility may, for example, be arranged at a distance from one another such that the first movement facility and the at least one further movement facility may accept the same medical instrument. For example, the first movement facility and the at least one further movement facility may be arranged in a longitudinal direction of the medical instrument. The first movement facility and the at least one further movement facility may further be arranged at a distance from one another along the path of the medical instrument running in a curve.

In addition, the first movement facility and the at least one further movement facility may be embodied for coordinated movement of the medical instrument. A coordinated movement may, for example, include a movement matched to the state of the medical instrument and/or to a state of the first movement facility and/or the at least one further movement facility and/or a matched movement sequence. Further, the movement of the medical instrument may, for example, be coordinated as a function of a state of the first movement facility and/or of the at least one further movement facility. The movement of the medical instrument may further be coordinated as a function of a state of the medical instrument. In one embodiment, the coordination facility may include a processing unit that is embodied for coordination of the movement of the medical instrument. In this case, the processing unit may be embodied for control of the first movement facility and/or of the at least one further movement facility.

The coordination facility may further have a movement sensor that is embodied to detect a movement of the medical instrument relative to the first movement facility and to at least one further movement facility. In this case, the further movement sensor may include an optical and/or electromagnetic and/or ultrasound-based movement sensor, for example. For example, the movement sensor of the coordination facility may be embodied as a mono camera and/or stereo camera. Provided the medical instrument has a marker structure and/or at least one marker object, the further movement sensor may detect the coordinated movement of the medical instrument based on the movement of the marker structure and/or of the at least one marker object. In this case, the movement sensor may be arranged on the first movement facility and/or on the at least one further movement facility, for example.

In a further form of embodiment of the coordination facility, the coordination of the movement of the medical instrument by the first movement facility and/or the at least one further movement facility may include a compensation for a torsion and/or deformation of the medical instrument.

With the medical instrument, a movement (e.g., rotation and/or translation) of at least one section of the medical instrument may result in a deformation (e.g., by compression) and/or torsion of the at least one section and/or of a further section of the medical instrument. In one embodiment, the first movement facility and/or the at least one further movement facility may be moved in a coordinated manner in such a way that a torsion and/or deformation is avoided and/or compensated for.

For example, the first movement facility may be opened and/or closed as a function of whether the at least one further movement facility is open or closed. Through this a free movement of the medical instrument, which is held by the first movement facility and/or the at least one further movement facility through the respective opened movement facility may be made possible. A course (e.g., a known course) of the surgical instrument between the first movement facility and/or the at least one further movement facility may be taken into account for coordination of the movement. For example, a course of the medical instrument at least curved in sections and/or running in a straight line may be taken into account for a rotation of the first movement facility and/or the least one further movement facility. A relative position of the first movement facility and/or of the at least one further movement facility and/or a distance between the first movement facility and the at least one further movement facility during a movement of the medical instrument may be taken into account.

In a further form of embodiment of the coordination facility, the coordination facility may also include an instrument detection unit. In this embodiment, the instrument detection unit may be embodied for identification of the medical instrument accommodated in the first movement facility and the at least one further movement facility. The medical instrument may further be moved by the first movement facility and/or the at least one further movement facility as a function of a material property of the identified medical instrument.

In this embodiment, the instrument detection unit may include a camera (e.g., a mono camera and/or a stereo camera) and/or a barcode scanner and/or an RFID detection unit and/or an electromagnetic antenna unit, for example. The medical instrument may also include at least one identifying property (e.g., a barcode and/or a marking and/or an RFID code and/or an electromagnetic transmitter unit). In one embodiment, the medical instrument may be identified by the instrument detection unit as soon as the medical instrument is arranged in the first movement facility and/or the at least one further movement facility and/or is approaching the facility.

In one embodiment, a material property of the medical instrument may be able to be obtained based on the identified medical instrument. In this case, the material property may include density information and/or hardness information and/or a deformation property and/or dimension information of the medical instrument. In one embodiment, the material property of the identified medical instrument may be taken into account for the coordinated movement of the first movement facility and/or the at least one further movement facility. For example, a speed of movement and/or a movement amplitude of the first movement facility and/or the at least one further movement facility may be able to be specified as a function of the material property of the identified medical instrument.

In a further form of embodiment of the coordination facility, the coordination facility may also include a state detection unit. In this embodiment, the state detection unit may be embodied to detect a deformation and/or torsion of the medical instrument. In this embodiment, the medical instrument may be moved by the first movement facility and/or the at least one further movement facility as a function of the detected deformation and/or torsion.

In this embodiment, the medical instrument may exert a restoration force directed in opposition to the movement of the first movement facility. For example, the medical instrument may be arranged at least in sections on and/or in an object being examined. In this embodiment, a restoring force on the rest of the medical instrument may be exerted by friction forces between the object being examined and the section of the medical instrument arranged thereon and/or therein. Through this, a torsion and/or deformation of the medical instrument occur after a movement of the first movement facility, in which the medical instrument is also moved, at least in sections. For example, with an arrangement where the first movement facility is very far apart from the at least one further movement facility, it may be necessary to compensate for and/or minimize a torsion and/or deformation of the medical instrument that has occurred by a coordinated movement of the at least one further movement facility.

The state detection unit may include, for example, a camera (e.g., a mono camera and/or stereo camera) and/or an ultrasound sensor and/or an electromagnetic sensor and/or an optical sensor and/or a tactile sensor, for example. In one embodiment, the state detection is embodied to detect a deformation and/or torsion of the medical instrument. In this case, the deformation and/or torsion may be able to be detected, for example, dynamically and/or in sections (e.g., between the first movement facility and the at least one further movement facility) by the state detection unit. For example, the state detection unit may be arranged on the first movement facility and/or the at least one further movement facility.

In this embodiment, a torsion of the medical instrument may be able to be detected by a tactile sensor, for example (e.g., through a restoration force between medical instrument and the respective movement facility). A deformation and/or torsion of the medical instrument may further be able to be detected by an optical sensor and/or a camera as a result of a surface change of the medical instrument and/or a course of the medical instrument that is changed at least in sections.

In addition, the medical instrument may be moved by the first movement facility and/or the at least one further movement facility coordinated such that the deformation and/or torsion of the medical instrument detected by the state detection unit is compensated for and/or minimized. The deformation and/or torsion of the medical instrument detected by the state detection unit (e.g., momentarily) may be taken into account in the release of the first movement facility and/or the at least one further movement facility (e.g., of the respective holder facility). For example, a movement of the first movement facility and/or the at least one further movement facility (e.g., an opening of the respective holder facility) may be able to be inhibited or enabled as a function of the detected deformation and/or torsion of the medical instrument.

The at least one further movement facility may further be able to be moved in alignment with the first movement facility. Through this, a torsion and/or deformation of the medical instrument produced by a widely-spaced arrangement of the first movement facility in relation to the at least one further movement facility may be compensated for and/or minimized. In one embodiment, the at least one further movement facility is arranged closer to the object being examined, on which and/or in which at least sections of the medical instrument are arranged, than the first movement facility.

Through this, a material-friendly and safe movement of the medical instrument by the coordination facility may be made possible. A risk of injury for the object being examined may also be minimized.

In a further form of embodiment of the coordination facility, the first movement facility and the at least one further movement facility may be arranged so that the coordination facility may be moved by means of the respective fastening element along at least one common movement axis, for example, at a constant spacing from one another. In this case, the at least one common movement axis may run parallel to a longitudinal axis of the medical instrument. The fastening element may further be able to be coupled mechanically and/or magnetically in a movable manner (e.g., by a motor) to a rail system. Through this, a directed movement of the first movement facility and the at least one further movement facility (e.g., of the coordination facility) may be made possible.

A forward movement (e.g., translational movement) and/or a rotational movement of the medical instrument (e.g., over a great distance) may be made possible, where the first movement facility is able to be moved repeatedly (e.g., iteratively) over a comparatively smaller distance relative to the at least one further movement facility in a coordinated manner. In this case, the processing unit may be embodied to detect a spatial positioning of the first movement facility and the at least one further movement facility (e.g., relative to one another and/or relative to the object being examined). In this case, the spatial positioning may include information about the spatial alignment and/or position of the first movement facility and the at least one further movement facility.

In a further form of embodiment of the coordination facility, the coordination facility may also include a grip element. In this embodiment, the arrangement of the first movement facility and the at least one further movement facility along the at least one common axis of movement may be fastened movably to the grip element. The grip element may further be able to be held by operating personnel. In this embodiment, the grip element may include a holder and/or a housing and/or a rail system for movable fastening of the first movement facility and the at least one further movement facility. The grip element may further be embodied as a protrusion (e.g., an ergonomic protrusion) and/or cutout and/or a recess on a housing of the coordination facility. For example, the grip element may partly enclose the first movement facility and the at least one further movement facility. Through this, a coordinated movement of the medical instrument is made possible while the coordination facility is being held by an operator using the grip element. In this case, the restoration force necessary for movement of the medical instrument may be able to be transferred by the operator via the grip element to the first movement facility and/or to the at least one further movement facility.

Through this, a flexible use of the coordination facility may be made possible.

Through the forms of embodiment of the coordination facility described above, support for a medical operator in placement and/or guidance and/or movement of the medical instrument (e.g., within the framework of an intervention) may be made possible.

A method for coordination of a movement of a medical instrument by a coordination facility will be described below. The advantages of the method essentially correspond to the advantages of the coordination facility for coordinated movement of a medical instrument described by way of example above. Features, advantages, or alternate forms of embodiment mentioned here may likewise also be transferred to the other subject matter and vice versa.

In a further aspect, the present embodiments relate to a method for coordination of a movement of a medical instrument by a coordination facility. In act s1), the medical instrument may be arranged in the first movement facility and the at least one further movement facility. In this case, the medical instrument may be introduced, for example, into the respective opening of the holder facility of the first movement facility and the at least one further movement facility. The first movement facility and/or the at least one further movement facility may further be arranged on the medical instrument in such a way that the medical instrument is accommodated in the respective opening of the holder facility.

Further, in act s2), a first position of at least one section of the medical instrument is determined. In this case, for example, a marking and/or a marker object on the medical instrument may be used for determining the first position. The first position may be determined relative to a reference point in space and/or relative to the first movement facility and/or relative to the at least one further movement facility and/or relative to an object being examined and/or relative to a medical imaging device. The first position may further be determined as the reference position of the medical instrument after the closure of the holder facility of the first movement facility and/or the at least one further movement facility.

In act s3), the first receiving element and/or the second receiving element of the holder facility of the first movement facility may be moved such that the at least three respective diaphragm elements hold the medical instrument. In this case, the holder facility of the first movement facility may be closed. In one embodiment, after act s3), the medical instrument may be held stably and firmly by the at least three diaphragm elements of the holder facility of the first movement facility.

Further, in act s4), there may be a movement of the first movement facility from an initial position into a target position, where at least sections of the medical instrument are moved as well. In this case, the first movement facility may, for example, be rotated and/or displaced in its entirety. In this case, the first movement facility may be displaced, for example, relative to at least one further movement facility. The holder facility of the first movement facility may further be rotated (e.g., relative to the first movement facility). In this case, at least sections of the medical instrument may be moved as well. This is made possible, for example, by the firm and stable holding of the medical instrument in the holder facility of the first movement facility. In one embodiment, the at least one further movement facility is opened during the movement of the first movement facility. Through this, it may be achieved that the medical instrument is accommodated freely movably in the at least one further movement facility during the movement of the first movement facility.

In act s5), a further position of the at least one section of the medical instrument relative to the first movement facility may be determined. In this case, for example, an angle of rotation and/or a distance covered and/or a number of rotations may be determined as the further position (e.g., in relation to the first position and/or the reference position).

In addition, in act s6), the first receiving element and/or the second receiving element of the holder facility of the at least one further movement facility may be moved in such a way that the at least three respective diaphragm elements hold the medical instrument. In this case, the holder facility of the at least one further movement facility may be closed. In one embodiment, after act s6), the medical instrument may be held stably and firmly by the at least three diaphragm elements of the holder facility of the at least one further movement facility.

Further, in act s7), the first receiving element and/or the second receiving element of the holder facility of the first movement facility may be moved in such a way that the medical instrument is released by the at least three diaphragm elements. In this case, the holder facility of the first movement facility may be opened. In one embodiment, after act s7), the medical instrument may be accommodated freely movably in the first movement facility.

Hereafter, in act s8), there may be a movement of the first movement facility from the target position into a further initial position. In one embodiment, the further initial position may correspond to the initial position of the first movement facility from act s4). The further initial position may further be predetermined as the initial position in act s4). In addition, the acts s1) to s8) may be repeated (e.g., iteratively) until a target position of the at least one section of the medical instrument is reached. Through this, a forward movement and/or a rotational movement of the medical instrument (e.g., over a greater distance) may be made possible, where the first movement facility is moved repeatedly (e.g., iteratively) over a comparatively smaller distance. The movement of the first movement facility and the at least one further movement facility may further be coordinated such that an opening and closing of the respective holder facility takes place as a function of the respective other holder facility. Through this, a secure holding of the medical instrument (e.g., between two movement steps) within the coordination facility may be provided.

Described below is a method for optimized movement of a medical instrument using a coordination facility. The advantages of the method essentially correspond to the advantages of the coordination facility for coordinated movement of a medical instrument described by way of example above. Features, advantages, or alternate forms of embodiment mentioned here may likewise also be transferred to the other subject matter and vice versa.

In a further aspect, the present embodiments relate to a method for optimized movement of a medical instrument by a coordination facility. In this aspect, the coordination facility may include a state detection unit, which is embodied to detect a state of a torsion and/or deformation of the medical instrument. The state detection unit may include a camera (e.g., a mono camera and/or stereo camera) and/or an ultrasound sensor and/or an electromagnetic sensor and/or an optical sensor and/or a tactile sensor, for example. In one embodiment, the state detection is embodied to detect a deformation and/or torsion of the medical instrument. In this case, the deformation and/or torsion may be able to be detected, for example, dynamically and/or in sections (e.g., between the first movement facility and the at least one further movement facility) by the state detection unit. For example, the state detection unit may be arranged on the first movement facility and/or the at least one further movement facility.

In a first act t1), the medical instrument may be arranged in the first movement facility and the at least one further movement facility. In this case, the medical instrument may be introduced, for example, into the respective opening of the holder facility of the first movement facility and the at least one further movement facility. The first movement facility and/or the at least one further movement facility may further be arranged on the medical instrument such that the medical instrument is accommodated in the respective opening of the holder facility.

Further, in act t2), there may be a movement of the first receiving element and/or the second receiving element of the holder facility of the first movement facility and the at least one further movement facility such that the at least three respective diaphragm elements hold the medical instrument. In this case, the respective holder facility of the first movement facility and the at least one further movement facility may be closed. In one embodiment, after act s3), the medical instrument may be held stably and firmly by the at least three respective diaphragm elements of the holder facility of the first movement facility and the at least one further movement facility.

In act t3), an initial state of the torsion and/or deformation of the medical instrument may be detected by the state detection unit. In this case, the initial state of the torsion and/or deformation of the medical instrument may include a material property (e.g., a momentary material property) of the medical instrument. The initial state of the torsion, for example, may further be determined by a reconciliation between at least two sensors of the state detection unit. In this case, a sensor of the state detection unit may be arranged in each case on the first movement facility and the at least one further movement facility.

In act t4), the first movement facility may be moved from an initial position into a target position. In this case, at least sections of the medical instrument may be moved as well. In this case, the first movement facility may, for example, be rotated and/or displaced in its entirety. In this case, the first movement facility may be displaced, for example, relative to the at least one further movement facility. The holder facility of the first movement facility may further be rotated (e.g., relative to the first movement facility). In this case, at least sections of the medical instrument may be moved as well. This is made possible, for example, by the firm and stable holding of the medical instrument in the holder facility of the first movement facility.

Further, in act t5), an intermediate state of the torsion and/or deformation of the medical instrument may be detected by the state detection unit. In this case, the intermediate state of the torsion and/or deformation of the medical instrument may include a material property (e.g., a momentary material property) of the medical instrument. The intermediate state of the torsion, for example, may further be determined by a reconciliation between at least two sensors of the state detection unit. In this case, a sensor of the state detection unit may be arranged in each case on the first movement facility and the at least one further movement facility. In addition, the intermediate state of the torsion and/or deformation of the medical instrument may include information about a change and/or deviation of the torsion and/or deformation of the medical instrument compared to the initial state.

In act t6), there may be at least one movement of the further movement facility as a function of the movement of the first movement facility in act t4). In this case, at least sections of the medical instrument may be moved as well. In this case, the at least one further movement facility may, for example, be rotated and/or displaced in its entirety. The at least one further movement facility may, for example, be displaced relative to the first movement facility. The holder facility of the at least one further movement facility may further be rotated (e.g., relative to the at least one further movement facility). In this case, at least sections of the medical instrument may be moved as well. This is made possible, for example, by the firm and stable holding of the medical instrument in the holder facility of the first movement facility.

Further, in act t7), a further intermediate state of the torsion and/or deformation of the medical instrument may be detected by the state detection unit. Further, through the movement of the at least one further movement facility in act t6), a deviation between the further intermediate state and the initial state may be minimized.

In this case, the at least one further movement facility may be moved in alignment with the first movement facility. Through this, a torsion and/or deformation of the medical instrument produced by a widely spaced arrangement of the first movement facility in relation to the at least one further movement facility may be compensated for and/or minimized. In one embodiment, the at least one further movement facility is arranged closer to the object being examined, which is able to be influenced by the medical instrument, than the first movement facility.

The proposed methods may, for example, be useful for assisting an operator during a movement and/or guidance and/or alignment of a medical instrument.

A computer program product that includes a program and is able to be loaded directly into a memory of a programmable processor unit and has program means (e.g., libraries and auxiliary functions) for carrying out a proposed method when the computer program product is executed is further provided. The computer program product in this case may include software with a source code that still is to be compiled and linked or only is to be interpreted, or executable software code, which still is to be loaded into the processing unit for execution. A proposed method may be carried out quickly, identically repeatedly, and robustly by the computer program product. The computer program product is configured so that the computer program product may carry out the process acts of the present embodiments by the processing unit. The processing unit in this case is to have the relevant required units, such as, for example, a corresponding main memory, a corresponding graphics card, or a corresponding logic unit, so that the respective method acts may be carried out efficiently.

The computer program product is stored, for example, on a computer-readable medium or is held on a network or server, from where the computer program product may be loaded into the processor of a processing unit, which is directly connected to the processing unit or may be embodied as part of the processing unit. Further, control information of the computer program product may be stored on an electronically-readable data medium. The control information of the electronically-readable data medium may be embodied such that, when the data medium is used in a processing unit, the control information carries out a method of the present embodiments. Examples of electronically-readable data media are a DVD, a magnetic tape, or a USB stick, on which electronically-readable control information (e.g., software) is stored. When this control information is read from the data medium and stored in a processing unit, all forms of embodiment of the methods described above may be carried out. Thus, the present embodiments may also be based on the computer-readable medium and/or the electronically-readable data medium.

Further forms of embodiment are described below.

In one embodiment, a movement facility for moving a medical instrument including a holder facility, a transmission element, and a connecting element is provided. The holder facility is embodied for holding the medical instrument. The transmission element transmits a movement between at least one part of the holder facility and the connecting element (e.g., bidirectionally). The connecting element is arranged at a distance from the holder facility.

In one embodiment, the transmission element has at least one belt drive and/or toothed drive.

In one embodiment, the holder facility has a number of degrees of freedom of movement. The transmission element transmits the movement according to the number of degrees of freedom of movement between the holder facility and the connecting element (e.g., bidirectionally and/or simultaneously).

In one embodiment, the connecting element has a connection receptacle for each of the degrees of freedom of movement of the holder facility.

In one embodiment, the movement facility further includes a housing. The housing encloses the holder facility and the transmission element such that the medical instrument is able to be introduced into the holder facility.

In one embodiment, the movement facility further includes a fastening element. The fastening element is embodied for fastening the movement facility to a medical device and/or a patient support facility.

In one embodiment, the fastening element has a motor drive that is embodied to move the movement facility.

In one embodiment, the movement facility includes a motor element. The motor element is embodied to be linked to the connecting element (e.g., mechanically), such that the motor element and the connecting element are movement-coupled.

In one embodiment, the motor element includes a sensor element to detect a movement of at least one part of the holder facility.

In one embodiment, a method for moving a medical instrument by a first movement facility includes arranging (r1) the medical instrument in the first movement facility. A first position of at least one section of the medical instrument is determined (r2), and the first receiving element and/or the second receiving element of the holder facility of the first movement facility is moved (r3) such that the at least three diaphragm elements hold the medical instrument. The first movement facility is moved (r4) from an initial position into a target position. The medical instrument is moved as well, at least in sections. A further position of the at least one section of the medical instrument is determined (r5), and the first receiving element and/or the second receiving element of the holder facility of the first movement facility is moved (r6) such that the medical instrument is released by the at least three diaphragm elements. The acts r2) to r6) are repeated until a target position of the at least one section of the medical instrument is reached.

In one embodiment, a coordination facility for coordinated movement of a medical instrument includes a first movement facility and at least one further movement facility. The first movement facility and the at least on further movement facility are arranged spaced at a distance from one another. The first movement facility and the at least one further movement facility are embodied for moving the same medical instrument. The first movement facility and the at least one further movement facility move the medical instrument in a coordinated manner.

In one embodiment, the coordination of the movement of the medical instrument by the first movement facility and/or the at least one further movement facility includes compensating for the torsion and/or deformation of the medical instrument.

In one embodiment, the coordination facility further includes an instrument detection unit that is embodied for identification of the medical instrument accommodated in the first movement facility and the at least one further movement facility. The medical instrument is moved by the first movement facility and/or the at least one further movement facility depending on a material property of the identified medical instrument.

In one embodiment, the coordination facility further includes a state detection unit. The state detection unit is embodied for detecting a deformation and/or torsion of the medical instrument. The medical instrument is moved by the first movement facility and/or the at least one further movement facility depending on the detected deformation and/or torsion.

In one embodiment, the coordination facility includes the first movement facility and the at least one further movement facility. The first movement facility and the at least one further movement facility are arranged movably along at least one common axis of movement (e.g., at a constant distance from one another).

In one embodiment, the coordination facility further includes a grip element. The first movement facility and the at least one further movement facility are fastened movably to the grip element along the at least one common axis of movement. The grip element is able to be gripped by an operator.

In one embodiment, a method for coordination of a movement of a medical instrument by a coordination facility includes arranging (s1) the medical instrument in the first movement facility and the at least one further movement facility. A first position of at least one section of the medical instrument is determined (s2), and the first receiving element and/or the second receiving element of the holder facility of the first movement facility is moved (s3) such that the at least three diaphragm elements hold the medical instrument in each case. The first movement facility is moved (s4) from an initial position into a target position. The medical instrument is moved as well at least in sections. A further position of the at least one section of the medical instrument is determined (s5), and the first receiving element and/or the second receiving element of the holder facility of the at least one further movement facility is moved (s6) such that the at least three diaphragm elements hold the medical instrument in each case. The first receiving element and/or the second receiving element of the holder facility of the first movement facility is moved (s7) such that the medical instrument is released by the at least three diaphragm elements. The first movement facility is moved (s8) from the target position into a further initial position. The further initial position is predetermined in act s4) as the initial position. The acts s1) to s8) are repeated until a target position of the at least one section of the medical instrument is reached.

In one embodiment, a method for optimized movement of a medical instrument by the coordination facility is provided. The coordination facility includes a state detection unit that is embodied to detect a state of a torsion and/or deformation of the medical instrument. The method includes arranging (t1) the medical instrument in the first movement facility and the at least one further movement facility. The first receiving element and/or the second receiving element of the holder facility of the first movement facility and the at least one further movement facility is moved (t2) such that the at least three diaphragm elements hold the medical instrument. An initial state of the torsion and/or deformation of the medical instrument is detected (t3) by the state detection unit. The first movement facility is moved (t4) from an initial position into a target position. The medical instrument is moved as well, at least in sections. An intermediate state of the torsion and/or deformation of the medical instrument is detected (t5) by the state detection unit, and the at least one further movement facility is moved (t6) depending on the movement of the first movement facility in act t4) and/or the intermediate state detected. The medical instrument is moved as well, at least in sections. A further intermediate state of the torsion and/or deformation of the medical instrument is detected (t7) by the state detection unit. Through the movement in act t6), a deviation between the further intermediate state and the initial state is minimized.

In one embodiment, a computer program product that includes a program and is able to be loaded directly into a memory of a programmable processor unit of a processing unit, with program means for carrying out a method, as, for example, described above, when the program is executed in the processor unit of the processing unit is provided.

BRIEF DESCRIPTION OF THE DRAWINGS

Exemplary embodiments are shown in the drawings and are described in greater detail below. In different figures, same reference characters are used for same features.

DETAILED DESCRIPTION

Figure 1:
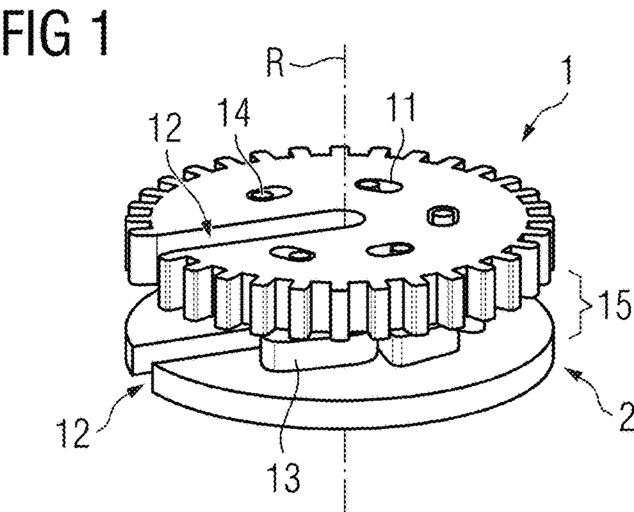
FIGS. 1 to 10 show schematic diagrams of different embodiments of a holder facility.

FIG. 1 schematically shows one embodiment of a holder facility (e.g., a holder). In this figure, the holder facility may include a first receiving element 1, a second receiving element 2, and at least three diaphragm elements 13. The at least three diaphragm elements 13 may further be arranged within a diaphragm layer 15 between the first receiving element 1 and the second receiving element 2 about a common axis of rotation R. In this figure, the common axis of rotation R may run essentially at right angles (e.g., not in parallel) to the diaphragm layer 15. In this figure, the first receiving element 1 and the second receiving element 2 may each have an opening 12 for receiving the medical instrument (not shown here). The first receiving element 1 and the second receiving element 2 may further be able to be moved about the common axis of rotation R relative to one another. The at least three diaphragm elements 13 may each have at least one first coupling element 14. The first receiving element 1 and/or the second receiving element 2 may include at least a second coupling element 11 in each case for each of the at least three diaphragm elements 13. In this figure, each of the at least three diaphragm elements 13 may be forcibly guided within the diaphragm layer 15 in which the elements are arranged by mechanical coupling between the respective at least one first coupling element 14 of the diaphragm element 13 and the at least one second coupling element 11. Further, for a movement of the first receiving element 1 relative to the second receiving element 2 about the common axis of rotation R, there may be a movement of the at least three diaphragm elements 13 within the diaphragm layer 15 towards the opening 12 for receiving the medical instrument forcibly guided by the first receiving element 1 and the second receiving element 2 such that the at least three diaphragm elements 13 hold a medical instrument arranged in the opening 12 of the first receiving element 1 and the second receiving element 2.

In the exemplary embodiment shown schematically in FIG. 1, the holder facility includes five diaphragm elements 13, for example. In this figure, the first receiving element 1 may include a second coupling element 11 in each case for each of the at least three diaphragm elements 13. The second coupling element 11 is cut out as an elongated guide and runs in a straight line. The second receiving element 2 may include a second coupling element (not shown) in each case for each of the at least three diaphragm elements 13. The second coupling element of the second receiving element 2 is cut out as an elongated guide and runs in a curve. The first receiving element 1 and the second receiving element 2 may further be embodied in the shape of a wheel. In this figure, the first receiving element 1 given as an example may be embodied as a toothed wheel. The opening 12 for receiving the medical instrument of the first receiving element 1 and the second receiving element 2 may further be embodied as a slot and be delimited by the common axis of rotation R. The at least three diaphragm elements 13 may further have a triangular shape. In this figure, each of the at least three diaphragm elements 13 may further have two first coupling elements 14 in each case, which may be embodied as pin-shaped raised areas. In this figure, a first of the two first coupling elements 14 of each of the at least three diaphragm elements 13 in each case may be arranged on a side of the diaphragm element 13 facing towards the first receiving element 1. A second of the two first coupling elements 14 of each of the at least three diaphragm elements 13 in each case may further be arranged on a side of the diaphragm element 13 facing towards the second receiving element 2. In this figure, the two first coupling elements 14 of each of the at least three diaphragm elements 13 may not lie on a spatial axis parallel to the common axis of rotation R.

In this figure, the holder facility may be embodied to save space and/or with modular components. The holder facility may further be embodied to hold different elongated medical instruments. The holder facility may further be embodied as an iris diaphragm, including the at least three diaphragm elements 13. In accordance with a further embodiment of the holder facility, the at least one first coupling element 14 of the respective diaphragm element 13 and/or the at least one second coupling element 11 of the first receiving element 1 and/or the second receiving element 2 may be embodied as a shoulder screw. In this figure, the mechanical coupling between at least one first coupling element 14 and at least one second coupling element 11 may be made by a forced guidance of the shoulder screw in an elongated guide.

There may further be a more even hold on the medical instrument with a higher number of diaphragm elements 13.

In one embodiment, a diameter of the opening 12 of the first receiving element 1 and the second receiving element 2 is proportional to a rotational movement of the first 1 receiving element relative to the second receiving element 2 about the common axis of rotation R.

This enables differently embodied medical instruments (e.g., heart catheters in particular various sizes in accordance with the French catheter system, and/or catheters for intracardial echocardiography, such as intracardiac-echo (ICE), and/or guide wires) to be held by the same holder facility. In this figure, the diameter of the medical instruments may range from the sub millimeter range (e.g., coronary guide wires with a diameter of 0.25 mm) through the millimeter range (e.g., ICE catheters with a diameter of 3.3 mm) to the centimeter range (e.g., bronchoscopes and/or laparoscopes with a diameter of over 14 mm). In this figure, the holder facility may be embodied for holding a large bandwidth of diameters of medical instruments (e.g., medical instruments with diameters between 0.25 mm and 14 mm). The holder facility may be embodied for holding medical instruments of a predetermined bandwidth of diameters (e.g., various guide wires with diameters in the sub millimeter range and/or various catheters with diameters in the millimeter range and/or various endoscopes with diameters in the centimeter range). This enables a space requirement (e.g., a spatial extent) of the holder facility to be minimized depending on application.

Figure 2:
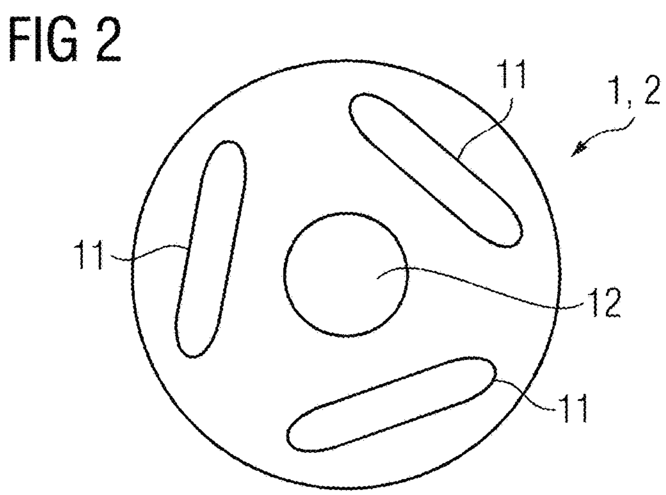

Shown schematically in FIG. 2 is a form of embodiment of the first receiving element 1 and/or the second receiving element 2. In this figure, the opening 12 for receiving the medical instrument is embodied by way of example as a hole. The at least one second coupling element 11 of the first receiving element 1 and/or the second receiving element 2 may further be embodied as an elongated guide, in which the at least one first coupling element 14 of respective diaphragm element 13 is accommodated in each case. In this figure, the elongated guides of the first 1 and/or the second receiving element 2 may be embodied as cutouts.

Figure 3:
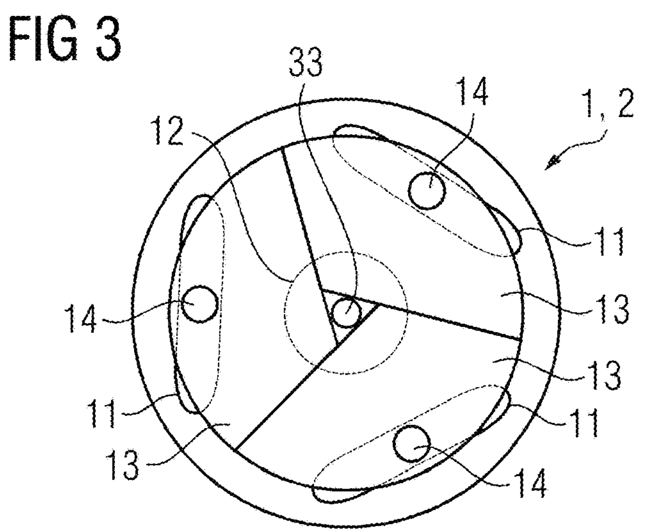

Shown schematically in FIG. 3, by way of example, is a further form of embodiment of the first receiving element 1 and/or the second receiving element 2 with three diaphragm elements 13. In this figure, each of the three diaphragm elements 13 may have two first coupling elements 14 in each case, which are embodied as raised areas (e.g., pin-shaped raised areas). The first receiving element 1 and/or the second receiving element 2 may further include a second coupling element 11 in each case for each of the first coupling elements 14 of the three diaphragm elements 13, which is cut out as an elongated guide. The three diaphragm elements 13 may have a circle segment shape along the diaphragm layer 15. In addition, the three diaphragm elements 13 may be arranged in the same shape about the common axis of rotation R. This enables an especially even hold on a medical instrument 33 arranged in the opening 12 of the first receiving element 1 and the second receiving element 2 to be made possible.

Figure 4:
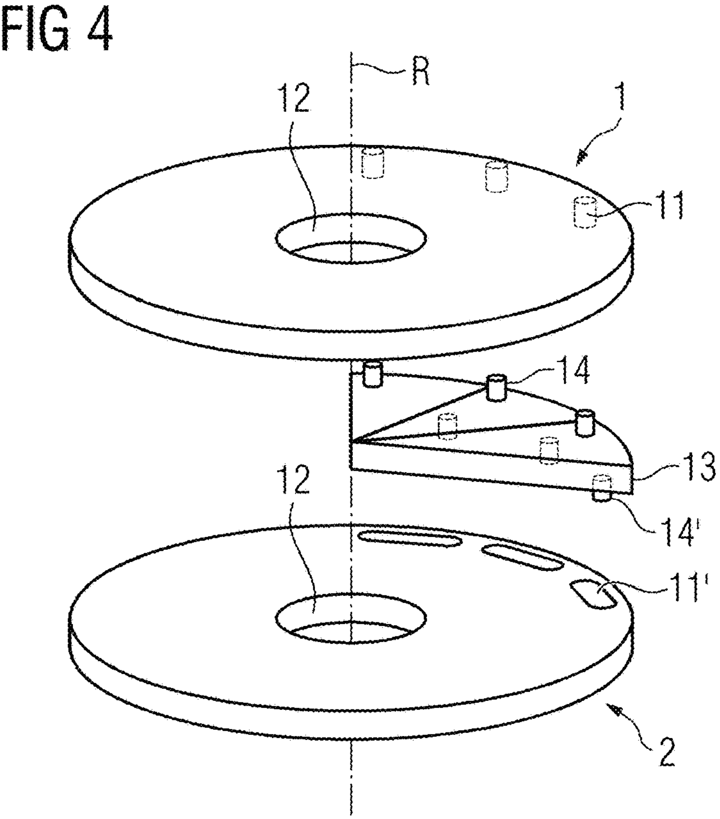

Shown schematically in FIG. 4 in an exploded diagram of one embodiment of the holder facility. In this figure, each of the at least three diaphragm elements 13 may include two first coupling elements 14 and 14' embodied as raised areas (e.g., in the shape of pins). The first receiving element 1 may further include a second coupling element 11 cut out as a hole for receiving a first coupling element 14 of a diaphragm element 13 in each case. This enables a mechanical coupling between the at least three diaphragm elements 13 and the first receiving element 1 to be achieved such that each of the at least three diaphragm elements 13 within the diaphragm layer 15 is supported rotatably. The second receiving element 2 may further have a second coupling element 11' cut out as an elongated guide in each case for receiving a first coupling element 14' of a respective diaphragm element 13 in each case. This enables a mechanical coupling between the at least three diaphragm elements 13 and the second receiving element 2 to be achieved such that each of the at least three diaphragm elements is forcibly guided within the diaphragm layer towards the opening 12 for receiving the medical instrument 33.

Figure 5:
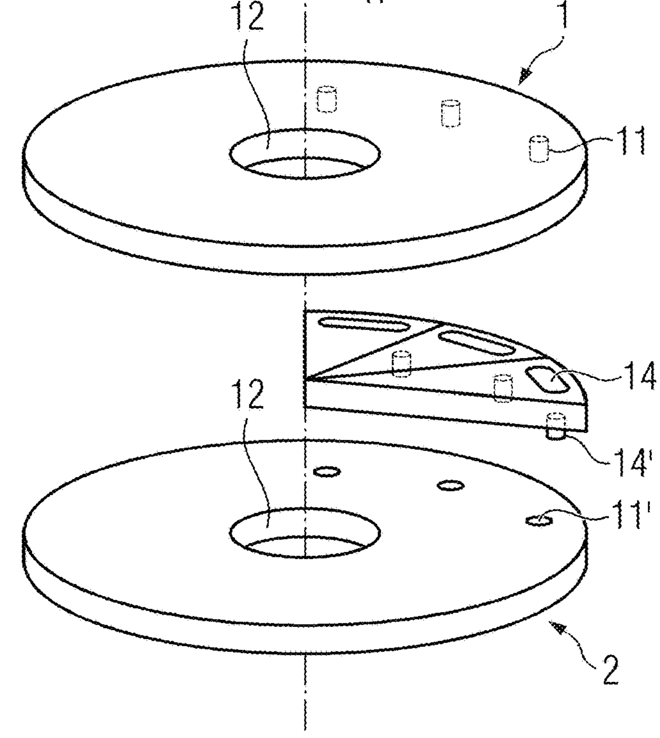

Shown schematically in FIG. 5 in an exploded diagram is another embodiment of the holder facility. In this figure, each of the at least three diaphragm elements 13 may have a first coupling element 14' in each case embodied as a, for example, pin-shaped raised area on a side facing towards the second receiving element 2. Each of the at least three diaphragm elements 13 may also have a first coupling element 14 cut out as an elongated guide on a side facing towards the first receiving element 1. In this figure, the first receiving element 1, for each of the at least three diaphragm elements 13, may have a second coupling element 11 embodied in each case as a pin-shaped raised area, which is accommodated in a first coupling element 14 (e.g., an elongated guide) of a diaphragm element in each case. The second receiving element 2, for each of the at least three diaphragm elements 13, may further have a second coupling element 11' cut out as a hole in each case, in which the coupling element 14' of a diaphragm element 13 in each case facing towards the second receiving element 2 is accommodated. This enables a mechanical coupling between the at least three diaphragm elements 13 and the second receiving element 2 to be achieved such that each of the at least three diaphragm elements 13 is supported rotatably within the diaphragm layer 15. The mechanical coupling between the at least three diaphragm elements 13 and the first receiving element 1 further enables a forcibly-guided movement of the at least three diaphragm elements 13 within the diaphragm layer towards the opening 12 for receiving the medical instrument 33 to be provided.

Figure 6:
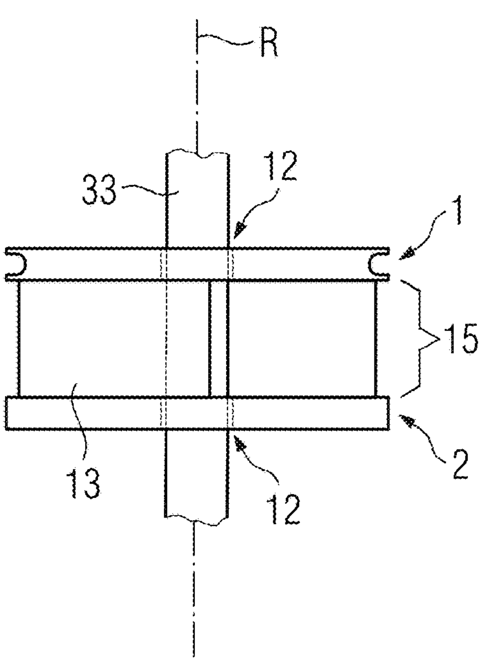

FIG. 6 shows a schematic of a side view of one embodiment of a holder facility. In this figure, the first receiving element 1 and the second receiving element 2 may be embodied in the shape of a wheel and may be arranged in parallel to one another. A medical instrument 33 may further be arranged in parallel to the common axis of rotation R within the opening 12 of the first receiving element 1 and the second receiving element 2. In this figure, the medical instrument 33 may be held by the at least three diaphragm elements 13, which are arranged within the diaphragm layer 15. In this figure, the first receiving element 1 is embodied as a pulley wheel. For example, the first receiving element 1 may have a cutout around a circumference of the first receiving element 1 to accept a belt.

Figure 7:
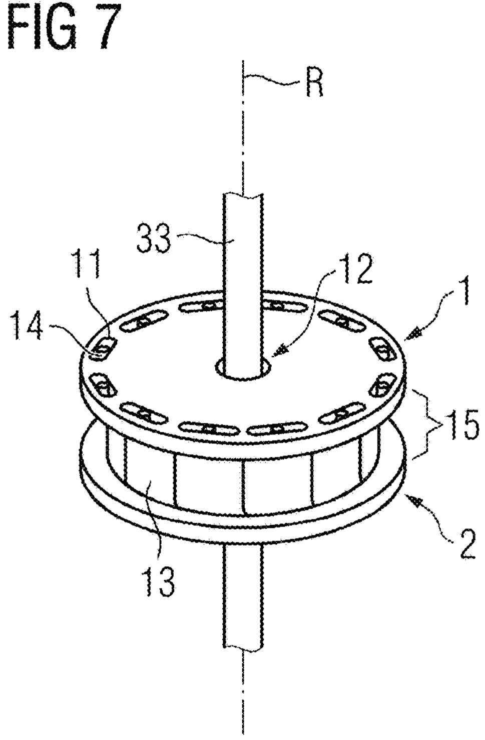

Shown schematically and perspectively in FIG. 7 is an embodiment of the holder facility. In this figure, the opening 12 for receiving the medical instrument 33 may be embodied as a hole. The medical instrument 33 may further be held by the at least three diaphragm elements 13 after the holder facility is closed. In this figure, the at least three diaphragm elements 13 may feature a softer material compared to the first receiving element 1 and/or the second receiving element 2. In one embodiment, a grip surface of the respective diaphragm element 13 may feature a non-slip material and/or adhesive material. Through this, a secure hold on the medical instrument 33 by the at least three diaphragm elements 13 can be made possible. In this figure, the at least three diaphragm elements 13 may consist at least partly of a softer material compared to the first receiving element 1 and/or the second receiving element 2 (e.g., visco foam and/or rubber). The at least three diaphragm elements 13 along the diaphragm layer 15 may have a triangular shape.

Figure 8:
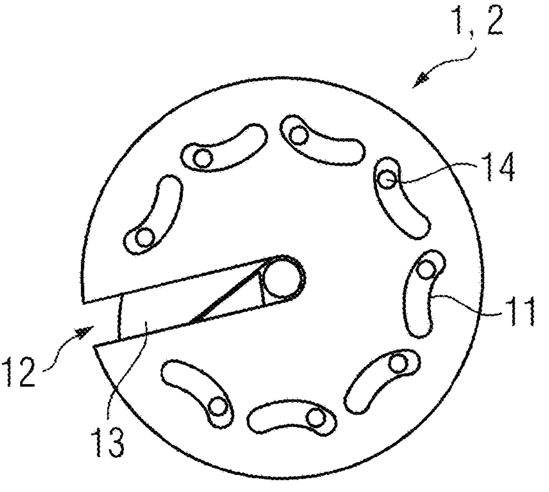

Shown schematically in FIG. 8 is another embodiment of the holder facility. In this figure, the opening 12 for receiving the medical instrument 33 of the first receiving element 1 and/or the second receiving element 2 may be embodied as a slot. This enables the medical instrument 33 to be introduced into the holder facility from the side. The holder facility (e.g., the first receiving element 1 and/or the second receiving element 2) may further be able to be put onto the medical instrument 33. In the form of embodiment shown in FIG. 8, the first receiving element 1 and/or the second receiving element 2 for each of the at least three diaphragm elements 13 may include a second coupling element 11 cut out as an elongated guide. In this figure, the second coupling elements 11 may, for example, run in a curve. Each of the at least three diaphragm elements in each case may further have at least one first coupling element 14 embodied as a pin-shaped raised area, which is accommodated in one of the second coupling elements 11 of the first receiving element 1 and/or the second receiving element 2 in each case. This enables the forcibly-guided movement of the at least three diaphragm elements 13 through to the opening 12 for receiving the medical instrument 33 (e.g., along a path predetermined by the curved course of the second coupling elements 11) to take place.

Figure 9:
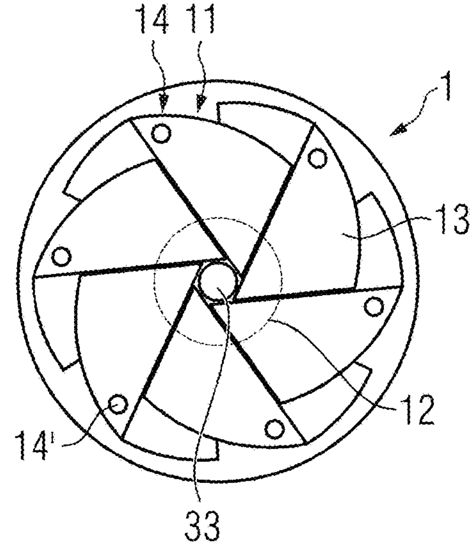

In the exemplary embodiment of the holder facility shown schematically in FIG. 9, the first receiving element 1 and the receiving element 2, for each of the at least three diaphragm elements 13, may include a second coupling element 14 embodied in each case as a raised area on an edge and/or a side surface. In this figure, the second coupling elements 14 embodied as a raised area may, for example, be connected to one another and/or at least partly enclose the diaphragm layer 15. The at least three diaphragm elements 13 may be at least partly enclosed by the second coupling elements 14 embodied as a raised area. Each of the at least three diaphragm elements 13 may have a first coupling element 13, in each case, that is embodied as a raised area and/or cutout on a side surface of the respective diaphragm element 13. In this figure, the mechanical coupling between the at least three diaphragm elements 13 and the first receiving element 1 may be made between the side surfaces of the diaphragm elements 13 and the second coupling elements 13 of the first receiving elements 1 embodied as a raised area in such a way that the at least three diaphragm elements 13 are forcibly guided through to the opening 12 for receiving the medical instrument 33. Each of the at least three diaphragm elements 13 may also include a first coupling element 14' embodied as a pin-shaped raised area and/or cut out as a hole for mechanical coupling to the second receiving element 2. This enables each of the at least three diaphragm elements 13 to be rotatably supported about the first coupling element 14' within the diaphragm layer 15.

Figures 10, 11, 12:
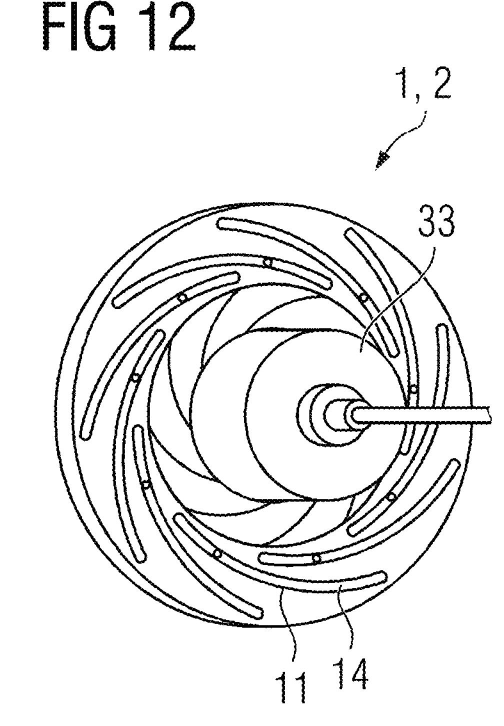
FIGS. 11 and 12 show a schematic diagram of an opened and a closed holder facility.

Depicted in FIG. 10 is yet another embodiment of the holder facility, where the at least three diaphragm elements 13 are arranged at least partly overlapping within the diaphragm layer 15. This enables a large number of diaphragm elements 13 to be arranged in a space-saving manner within the diaphragm layer 15. An even hold on the medical instrument 33 within the opening 12 may further be made possible by the at least three diaphragm elements 13.

Shown schematically in FIG. 11 is an embodiment of the holder facility, where a medical instrument 33 arranged in the opening 12 is able to be moved freely. The holder facility is opened for receiving the medical instrument 33. In this figure, the first coupling elements 14 of the at least three diaphragm elements 13 are in an initial position in relation to the second coupling elements 11. In FIG. 12, the holder facility is shown schematically in the closed state. In this figure, the medical instrument 33 arranged in the opening 12 is held by the at least three diaphragm elements 13. Through a movement of the first receiving element 1 relative to the second receiving element 2, the at least three diaphragm elements 13 have been forcibly guided such that the first receiving element 1 and the second receiving element 2 enclose the medical instrument 33.

Figure 13:
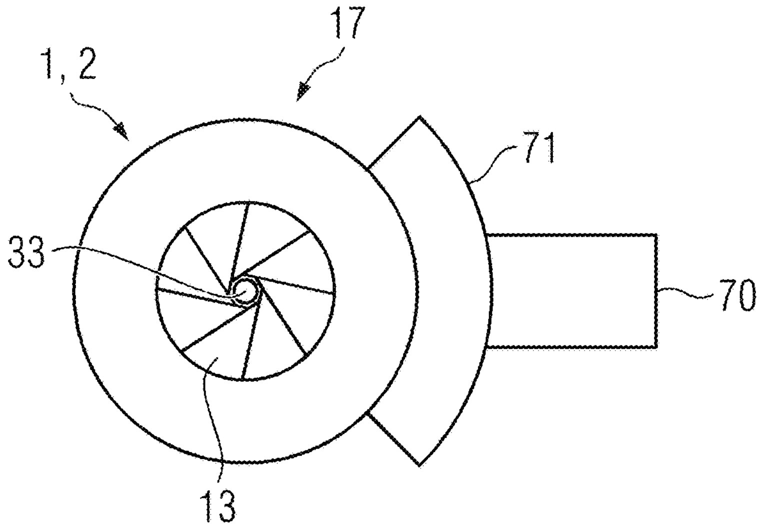
FIG. 13 shows a schematic diagram of an embodiment of a holder facility with a motorized drive element.

In the embodiment of the holder facility 17 shown schematically in FIG. 13, the holder facility 17 may also include a motorized drive element 70. In this figure, the motorized drive element 70 may be embodied to move the first receiving element 1 relative to the second receiving element 2 about the common axis of rotation R. In this figure, the motorized drive element 70 may include a motor (e.g., an electric motor). The motorized drive element 70 may further include a transmission element 71 that couples the motor mechanically to the first receiving element 1 and/or the second receiving element 2. In this figure, the transmission element 71 may be embodied as a belt and/or toothed wheel and/or transmission and/or leadscrew.

The medical instrument 33 is held firmly by the at least three diaphragm elements 13 for as long as the first receiving element 1 and the second receiving element 2 of the holder facility 17 remain at rest relative to one another in the closed state. In this figure, the holder facility 17 may also include a fixing element embodied to lock the first receiving element 1 in place in relation to the second receiving element 2. The first receiving element 1 may, for example, be locked in place in relation to the second receiving element 2 by the fixing element in the closed state of the holder facility 17. In this figure, the fixing element may, for example, be embodied as a lock (e.g., a lever and/or a plug connection between the first receiving element 1 and the second receiving element 2) and/or may be embodied as part of the motorized drive element 70.

Figure 14:
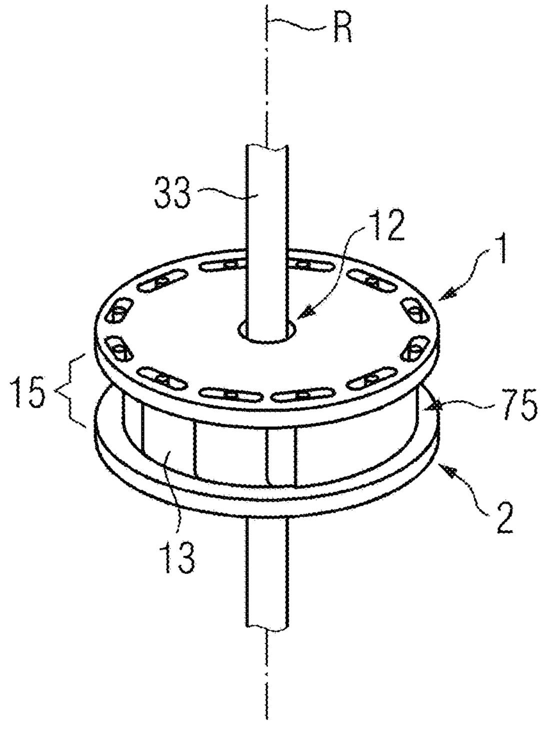
FIG. 14 shows a schematic diagram of an embodiment of a holder facility with a diaphragm fixing element.

Shown schematically in FIG. 14 is another embodiment of the holder facility 17. In this figure, the holder facility 17 may also include a diaphragm fixing element 75 embodied to lock the at least three diaphragm elements 13 in place. In this figure, the diaphragm fixing element 75 may be arranged within the diaphragm layer 15 and/or around the diaphragm layer 15. In one embodiment, at least one of the diaphragm elements 13 may be able to be locked in a fixed position by the diaphragm fixing element 75. The diaphragm fixing element 75 may further be embodied to mechanically rigidly couple the at least one first coupling element 14 of at least one diaphragm element 13 to the corresponding at least one second coupling element 11 of the first receiving element 1 and/or the second receiving element 2 (e.g., so that the receiving element 1, 2 does not move).

The diaphragm fixing element 75 may further be embodied to lock in place the arrangement of the at least three diaphragm elements 13 (e.g., in the closed state of the holder facility 17). In this figure, the diaphragm fixing element 75 may be embodied as a circumferential band and/or ring and/or lever and/or clamp. In one embodiment, the holder facility 17 may be opened by releasing the lock of the at least three diaphragm elements 13. With an arrangement of the diaphragm fixing element 13 within the diaphragm layer 15, a space-saving design may be made possible.

In one embodiment, through a locking of the at least three diaphragm elements 13 by the diaphragm fixing element 15, a movement of the first receiving element 1 and/or the second receiving element 2 may be made possible. In this figure, the first receiving element 1 and/or the second receiving element 2 may be able to be removed from the holder facility 17 after locking of the at least three diaphragm elements 13 by the diaphragm fixing element 75.

Figure 15:
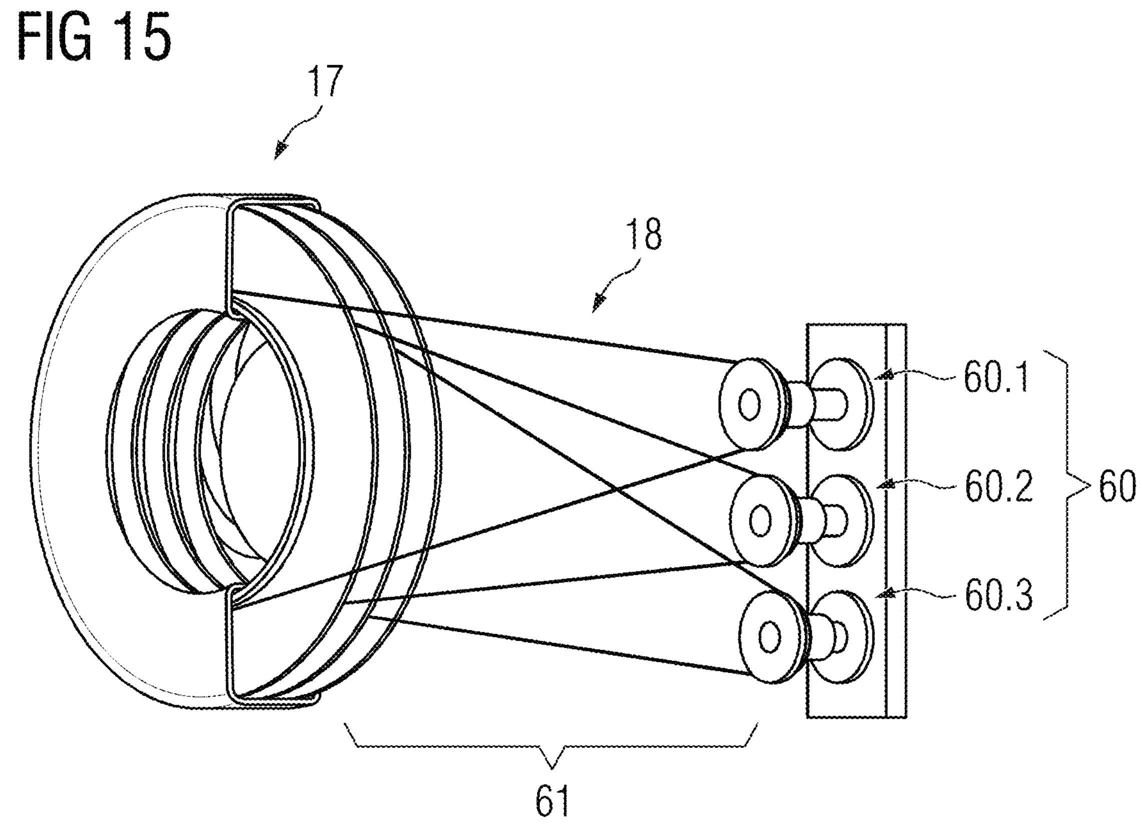
FIG. 15 shows a schematic diagram of an embodiment of a movement facility.

FIG. 15 shows a schematic diagram of one embodiment of a movement facility for movement of a medical instrument 33. In this figure, the movement facility may include a holder facility 17, a transmission element 61, and a connection element 60. The holder facility 17 may be further embodied for holding the medical instrument 33. In addition, the transmission element 61 may transmit a movement between at least one part of the holder facility 17 and the connection element 60 (e.g., bidirectionally). In this figure, the connection element 60 may be arranged at a distance from the holder facility 17.

In the embodiment of the movement facility 18 shown schematically in FIG. 15, the transmission element 61 may have a belt drive. In addition or as an alternative, the transmission element 61 may have a toothed wheel drive (not shown).

In addition, the holder facility 17 may have a number of degrees of freedom of movement (e.g., three degrees of freedom of movement). In this figure, the transmission element 61 may transmit the movement in accordance with the number of degrees of freedom of movement between the holder facility 17 and the connection element 60 (e.g., bidirectionally and/or simultaneously). The connection element 60 may further have a connection receptacle 60.1, 60.2 and 60.3 in each case for each of the degrees of freedom of movement of the holder facility 17. In this figure, the transmission element 61, for each of the three degrees of freedom of movement of the holder facility 17, for example, may have a belt drive in each case for transmission of the movement to one of the three connection receptacles 60.1, 60.2 and 60.3 in each case.

Figure 16:
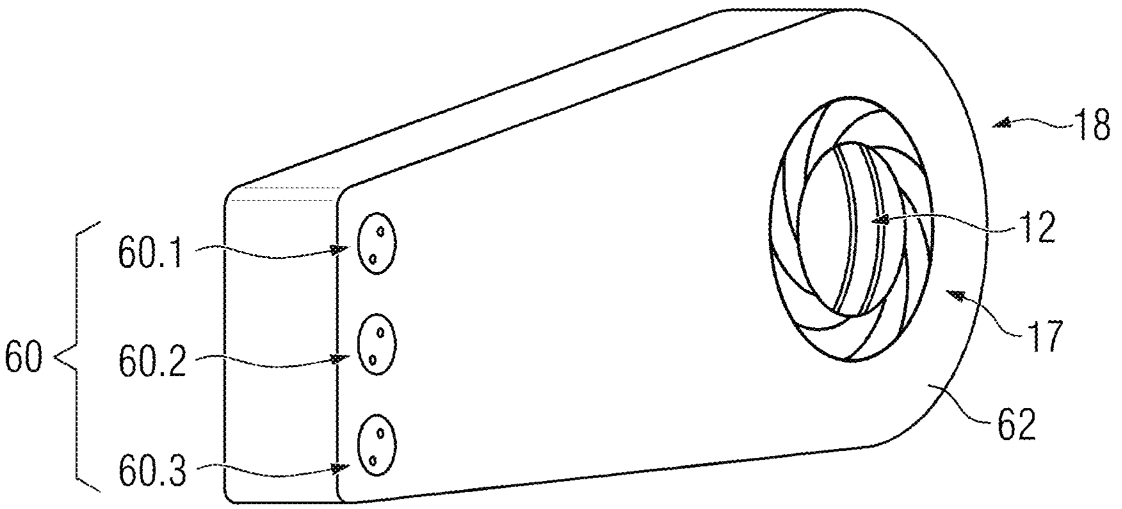
FIG. 16 shows a schematic diagram of an embodiment of a movement facility with a housing.

FIG. 16 shows a schematic diagram of one embodiment of a movement facility 18 with housing 62. In this figure, the movement facility 18 may include a housing 62 that encloses the holder facility 17 and the transmission element 61 such that the medical instrument 33 is able to be introduced into the holder facility 12 (e.g., into the opening 12 of the holder facility 12).

In one embodiment, the holder facility 17 and the transmission element 61 may be protected by the housing 62 against any mechanical and/or chemical influence. It can further be made easier by the housing 62 to clean the movement facility 18. In addition, a mechanical stability of the arrangement including the holder facility 17, the transmission element 61, and the connection element 60 may be improved by the housing 62. In the form of embodiment shown in FIG. 16, the housing 62 also includes an opening in each case for each of the connection receptacles 60.1, 60.2 and 60.3.

Figure 17:
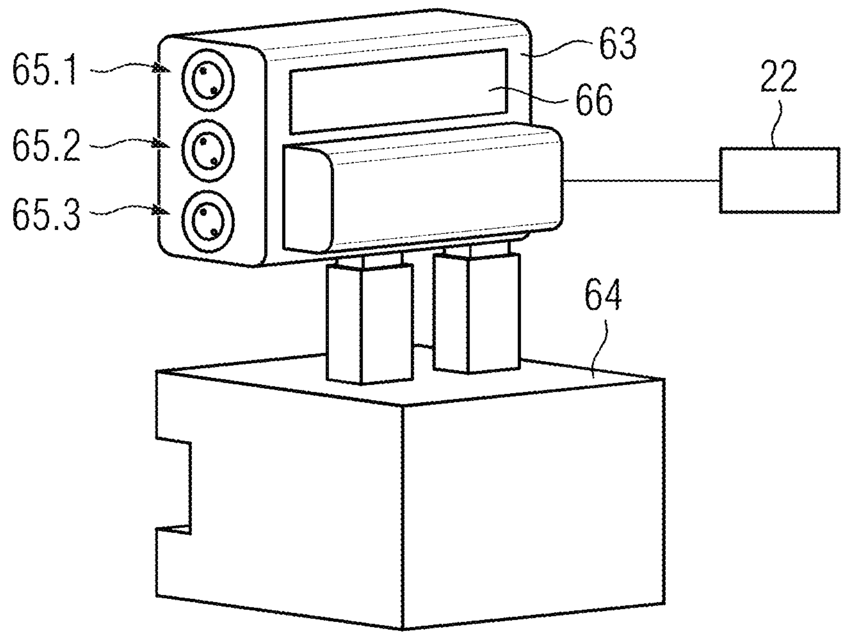
FIG. 17 shows a schematic diagram of one embodiment of a motor element and a fastening element.

Shown in FIG. 17 is a schematic diagram of one embodiment of a motor element 63 and a fastening element 64. In this figure, a movement facility 18 may include the motor element 63 and the fastening element 64. The fastening element 64 may further be embodied for fastening the movement facility 18 to a medical device and/or a patient support facility (e.g., to a guide rail). The motor element 63 may also be embodied to be connected to the connection element 60 (e.g., mechanically), in such a way that the motor element 63 and the connection element 60 are movement-coupled. This enables a movement to be able to be transmitted between the motor element 63 and at least one part of the holder facility 17 by the transmission element 60.

For example, the fastening element 64 may include a movement unit (e.g., a roller system). This enables a movement of the movement facility 18 to be made possible. In one embodiment, the movement unit of the fastening elements 64 may have a motor drive, where the processing unit 22 may further be embodied to control the motor drive.

In this figure, the motor element 63 may be embodied both to open and/or to close the holder facility 17, and also for movement of the holder facility 17 in its entirety. Through this, a rotational movement of the medical instrument 33 held in the holder facility 17 may be made possible. The motor element 63 may further be arranged on a side of the first receiving element 1 and/or the second receiving element 2 (e.g., along the common axis of rotation R). Through this, a space-saving arrangement may be made possible.

The motor element 63 may also include a sensor element 66 for detection of a movement of at least a part of the holder facility 17. In this figure, the sensor element 66 may include an optical and/or electromagnetic sensor, for example.

The holder facility 17, the transmission element 61, the connection element 60, and the housing 62 may further be embodied as a single-use cassette. In this figure, the motor element 63 and the fastening element 64 may be reusable, while the single-use cassette described is, for example, able to be coupled by the connection element to the motor element. In one embodiment, the single-use cassette may be embodied in a space-saving manner.

In addition, the movement facility 18 may include a processing unit 22 (e.g., a processor) that is embodied to control the motor element 63 and/or the holder facility 17.

Figure 18:
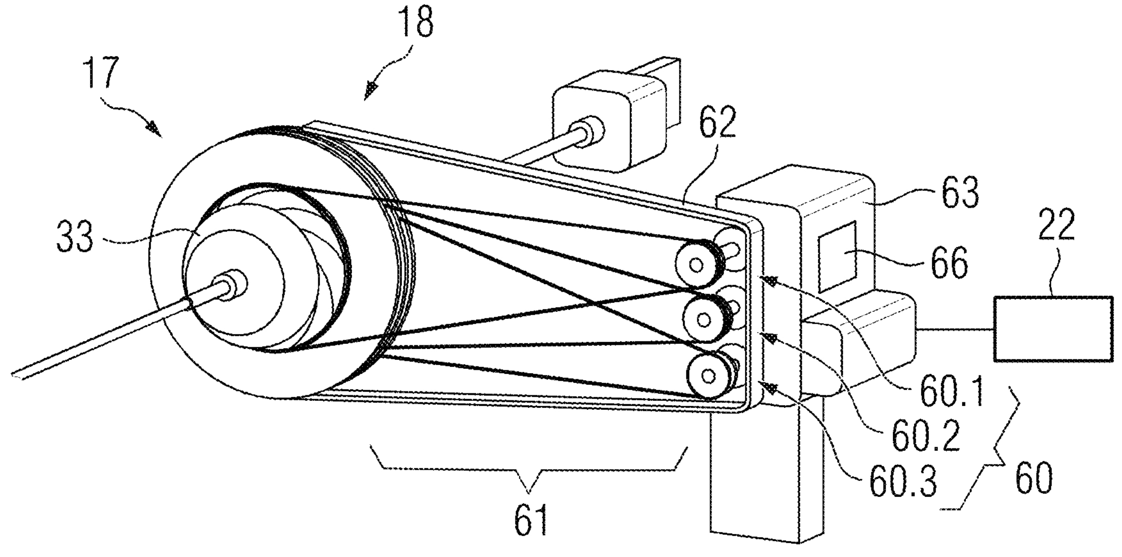
FIG. 18 shows a schematic diagram of one embodiment of a movement facility with a housing and a motor element.

Shown in FIG. 18 is a schematic diagram of one embodiment of a movement facility 18 with housing 62 and motor element 63. In this figure, the motor element 63 may be mechanically coupled to one of the three degrees of freedom of movement of the holder facility 17 in each case (e.g., using the three connection receptacles 60.1, 60.2 and 60.3). In this figure, the housing 62 may be embodied, for example, as a sterile barrier between the movement facility 18 and the motor element 63.

Figure 19:
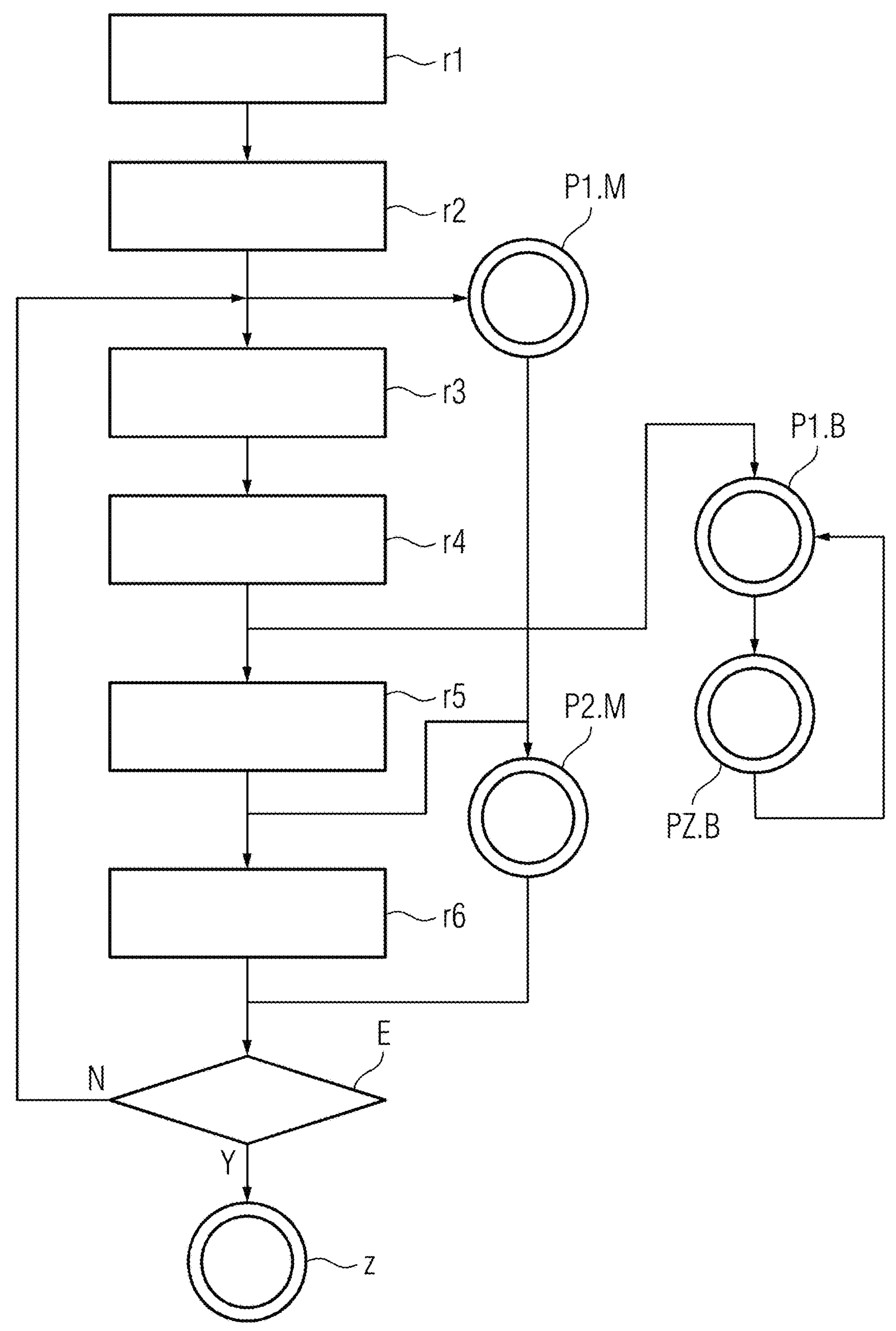
FIG. 19 shows a schematic diagram of a flowchart of one embodiment of a method for moving a medical instrument by a movement facility.

Depicted in FIG. 19 is a schematic diagram of one embodiment of a method for moving medical instruments using a first movement facility 18. Accordingly, in a first act r1), the medical instrument 33 may be arranged in the first movement facility 18. Further, in act r2), a first position P1.M of at least a section of the medical instrument 33 may be determined. Hereafter, in act r3), the first receiving element 1 and/or the second receiving element 2 of the holder facility 17 of the first movement facility 18 may be moved such that the at least three diaphragm elements 13 hold the medical instrument 33. In act r4), the first movement facility 18 may be moved from an initial position P1.B into a target position PZ.B, where at least a section of the medical instrument 33 is moved as well. In act r5), a further position P2.M of the at least one section of the medical instrument 33 may be determined. Further, in act r6), the first receiving element 1 and/or the second receiving element 2 of the holder facility 17 of the first movement facility 18 may be moved in such a way that the medical instrument 33 is released by the at least three diaphragm elements 13. In this figure, the acts r2) to r6) may be repeated until a target position Z of the at least one section of the medical instrument 33 is reached. In this figure (e.g., after act r6)), there may be a reconciliation E of the further position P2.M with the target position Z.

The method may, for example, be useful for automated movement and/or movement assisting an operator of the medical instrument 33 by the movement facility 18 towards target position Z. The method may also include a regulation of the movement by a signal of the sensor element 66 and/or visually-guided navigation (e.g., monitored by a medical imaging method, such as computed tomography angiography and/or magnetic resonance angiography and/or ICE ultrasonography and/or intravascular ultrasound (IVUS) and/or optical coherence tomography (OCT)).

Figure 20:
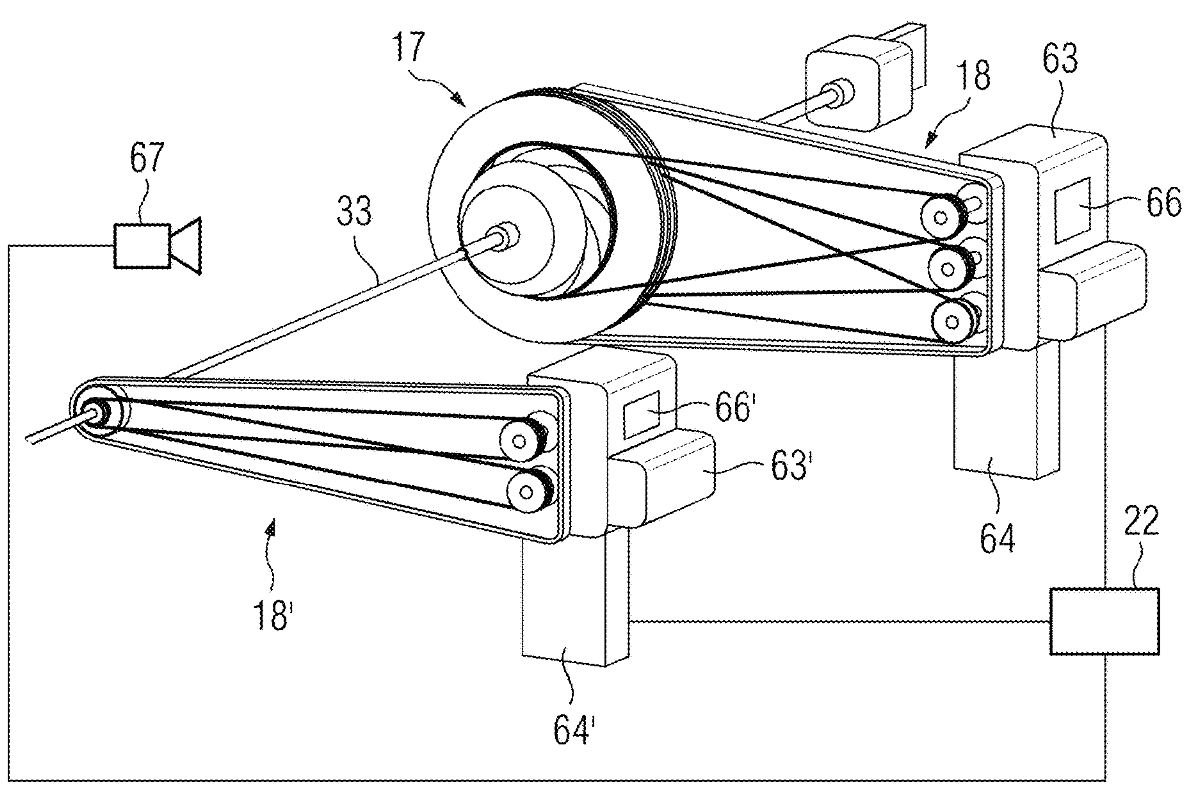
FIG. 20 shows a schematic diagram of one embodiment of a coordination facility for coordinated movement of a medical instrument.

Shown schematically in FIG. 20 is one embodiment of a coordination facility for coordinated movement of a medical instrument 33. In this figure, the coordination facility may include a first movement facility 18 and at least one further movement facility 18'. The first movement facility 18 and the at least one further movement facility 18' may further be arranged at a distance from one another. In this figure, the first movement facility 18 and the at least one further movement facility 18' may be embodied for moving the same medical instrument 33. The first movement facility 18 and the at least one further movement facility 18' may further move the medical instrument 33 in a coordinated manner. In this figure, the coordination facility may include a processing unit 22 for coordination of the movement of the first movement facility 18 and the at least one further movement facility 18'.

The coordination of the movement of the medical instrument 33 by the first movement facility 18 and/or the at least one further movement facility 18' may also include a compensation for a torsion and/or deformation of the medical instrument 33.

In addition, the coordination facility may also include an instrument detection unit 67 that is embodied for identification of the medical instrument 33 accommodated in the first movement facility 18 and the at least one further movement facility 18'. In this figure, the medical instrument 33 may be moved by the first movement facility 18 and/or the at least one further movement facility 18' as a function of a material property of the identified medical instrument 33. For this, the instrument detection unit 67 may send a signal to the processing unit 22, for example.

The coordination facility may include a state detection unit that is embodied to detect a deformation and/or torsion of the medical instrument 33. In this figure, the state detection unit may include a sensor element 66 for the first movement facility 18 and at least one further sensor element 66' for the at least one further movement facility 18' in each case. The medical instrument 33 may further be moved by the first movement facility 18 and/or the at least one further movement facility 18' as a function of the detected deformation and/or torsion. For this, the sensor elements 66 and 66' of the state detection unit may each send a signal to the processing unit 22.

In addition, the first movement facility 18 and the at least one further movement facility 18' may be arranged movably by a fastening element 64 and 64' (e.g., fasteners) in each case along at least one common movement axis (e.g., at a constant distance from one another).

Figure 21:
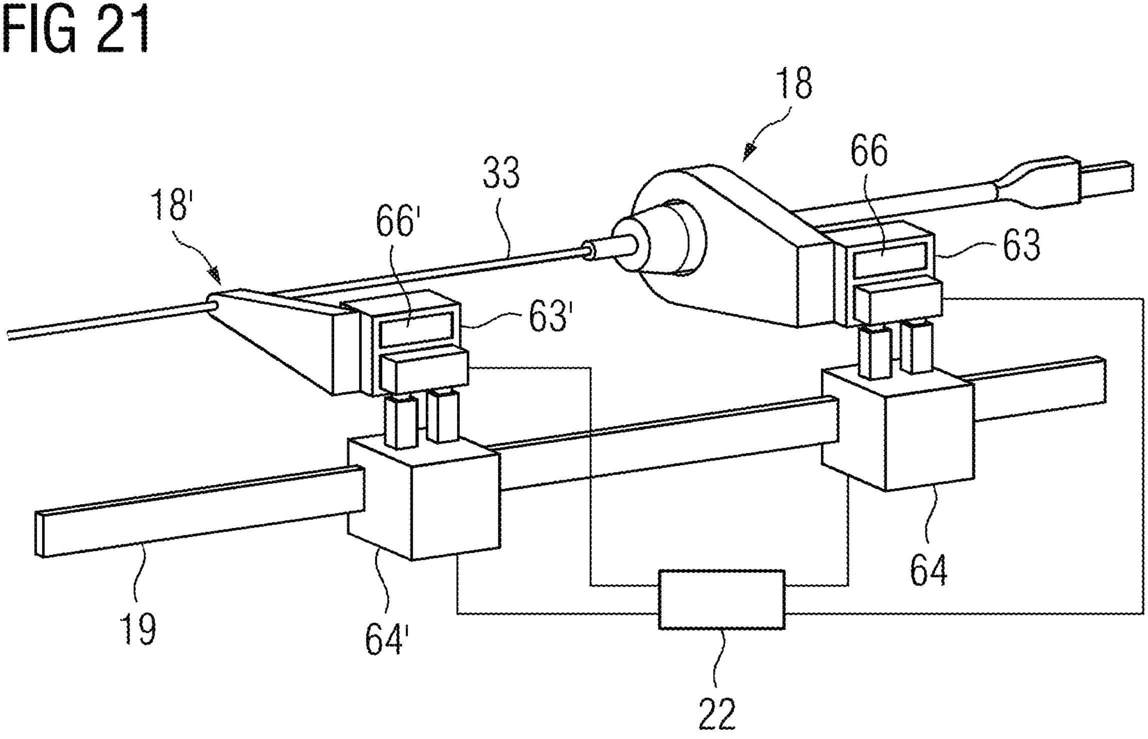
FIG. 21 shows a schematic diagram of another embodiment of a coordination facility.

Shown schematically in FIG. 21 is another embodiment of the coordination facility. In this figure, the first movement facility 18 and the at least one further movement facility 18' may be arranged movably by the respective fastening elements 64 and 64' on a common rail 19. For example, the fastening elements 64 and 64' may each include a movement unit (e.g., a roller system). Through this, a guided movement of the first movement facility 18 and the at least one further movement facility 18' along the common rail 19 may be made possible. In one embodiment, at least one of the movement units of the fastening elements 64 and 64' may have a motor drive, where the processing unit 22 may be further embodied for control (e.g., coordinated control) of the motor drive. In this figure, a movement unit of the fastening elements 64 and/or 64' may, for example, be able to be moved passively. The first movement facility 18 and the at least one further movement facility 18' may further be able to be enclosed (e.g., during an intervention) by sterile envelopes (e.g., a housing).

Figure 22:
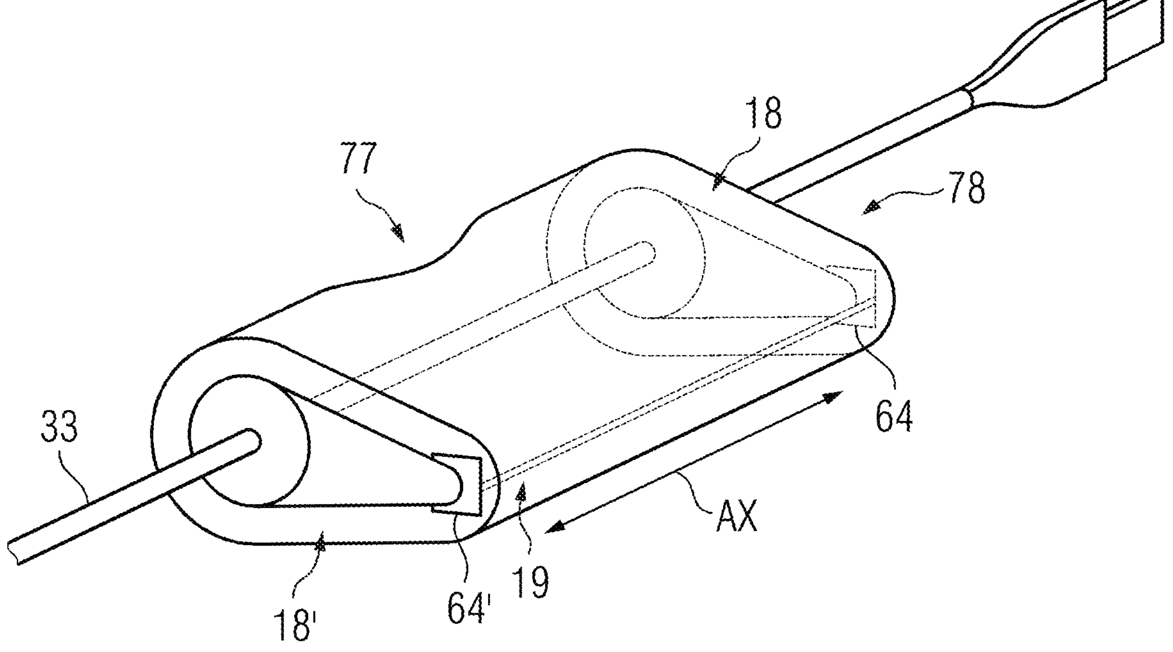
FIG. 22 shows a schematic diagram of one embodiment of a coordination facility with a grip element.

Shown schematically in FIG. 22 is yet another embodiment of the coordination facility. In this figure, the coordination facility may also include a grip element 77, where the arrangement of the first movement facility 18 and the at least one further movement facility 18' along the at least one common axis of movement AX are fastened movably to the grip element. In this figure, the grip element 77 may be able to be held by an operator. In one embodiment, the arrangement of the first movement facility 18 and the at least one further movement facility 18' may be able to be enclosed by a housing 78. In this figure, the housing 78 may further include the grip element 77 and/or be embodied as grip element 77.

Figure 23:
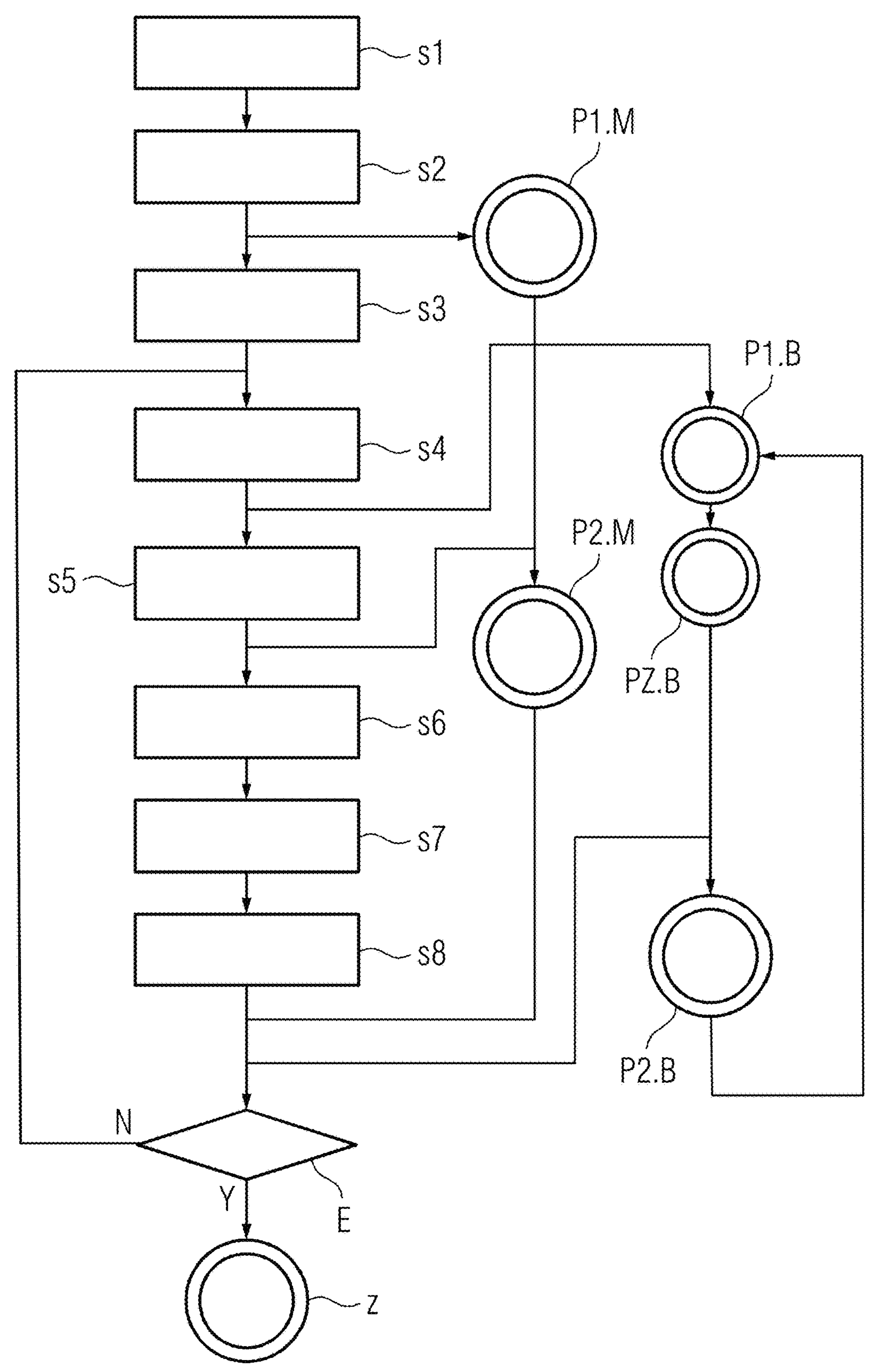
FIG. 23 shows a schematic diagram of a flowchart of one embodiment of a method for coordination of moving a medical instrument by a coordination facility.

Shown schematically in FIG. 23 is a flow diagram of one embodiment of a method for coordination of a movement of a medical instrument 33 by a coordination facility. In this figure, in a first act s1), the medical instrument 33 may be arranged in the first movement facility 18 and the at least one further movement facility 18'. In addition, in act s2), a first position P1.M of at least one section of the medical instrument 33 may be determined. Hereafter, in act s3), the first receiving element 1 and/or the second receiving element 2 of the holder facility 17 of the first movement facility 18 may be moved such that the at least three diaphragm elements 13 hold the medical instrument 33 in each case. Further, in act s4), the first movement facility 18 may be moved from an initial position P1.B into a target position PZ.B. In this figure, at least sections of the medical instrument 33 are moved as well. In act s5), a further position P2.M of the at least one section of the medical instrument 33 may be determined. In act s6), the first receiving element 1 and/or the second receiving element 2 of the holder facility 17 of the at least one further movement facility 18' may be moved such that at least three diaphragm elements 13 hold the medical instrument 33 in each case. Hereafter, in act s7), the first receiving element 1 and/or the second receiving element of the holder facility 17 of the first movement facility 18 may be moved such that the medical instrument 33 is released by the at least three diaphragm elements 13. In act s8), the first movement facility 18 may be moved from the target position PZ.B into a further initial position P2.B. In this figure, the further initial position P2.B in act s4) may be predetermined as initial position P1.B. The acts s1) to s8) may further be repeated until a target position Z of the at least one section of the medical instrument 33 is reached. In this figure, for example, after act s8), there may be a reconciliation E of the further position P2.M with the target position Z.

Through this, an almost infinite movement of the medical instrument 33 may be made possible. A movement trajectory of the medical instrument independent of a distance of the first 18 in relation to the at least one further movement facility 18' may be realized by repeatedly carrying out the acts s1) to s8).

Figure 24:
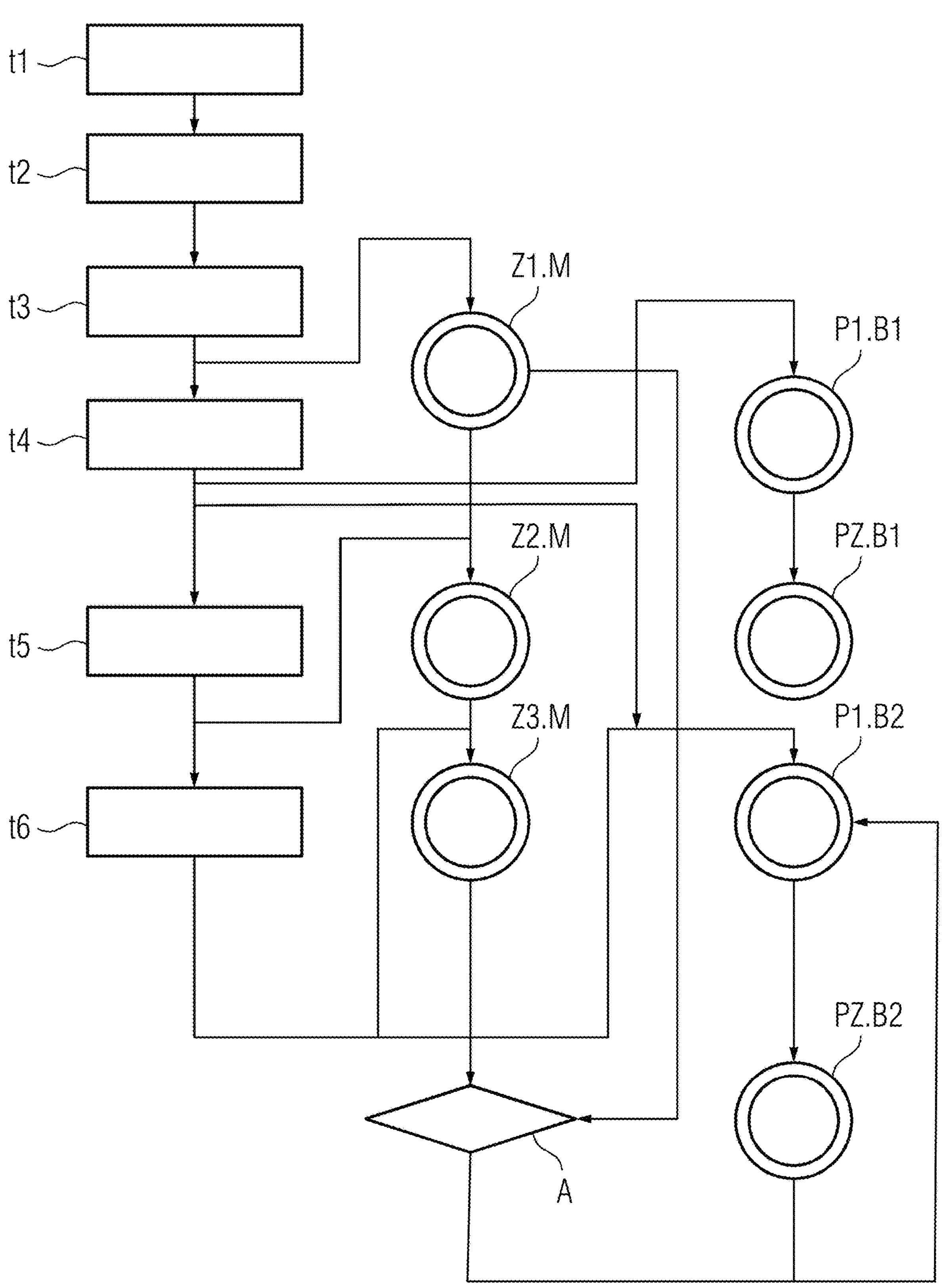
FIG. 24 shows a schematic diagram of a flowchart of one embodiment of a method for optimized movement of a medical instrument by a coordination facility.

Shown schematically in FIG. 24 is a flow diagram of an embodiment of a method for optimized movement of a medical instrument 33 by a coordination facility. In this figure, the coordination facility may include a state detection unit for detecting a state of a torsion and/or deformation of the medical instrument 33. In a first act t1), the medical instrument 33 may be arranged in the first movement facility 18 and the at least one further movement facility 18'. Hereafter, in act s2), the first receiving element 1 and/or the second receiving element 2 of the holder facility 17 of the first movement facility 18 and the at least one further movement facility 18' may be moved such that the at least three diaphragm elements 13 hold the medical instrument 33 in each case. In act s3), an initial state Z1.M of a torsion and/or deformation of the medical instrument 33 may be detected by the state detection unit. Hereafter, in act t4), there may be a movement of the first movement facility 18 from an initial position P1.B1 into a target position PZ.B1, where at least sections of the medical instrument 33 are moved as well. In act t5), an intermediate state Z2.M of a torsion and/or deformation of the medical instrument 33 may be detected by the state detection unit. Hereafter, in act t6), the at least one further movement facility 18' may be moved as a function of the movement of the first movement facility in act t4) and/or of the detected intermediate state Z2.M b. In this figure, the at least one further movement facility 18' may be moved from an initial position P1.B2 into a target position P2.B2. Further, in act t7) (e.g., after and/or during the movement of the at least one further movement facility 18' in act t6), a further intermediate state Z3.M of the at least one section of the medical instrument 33 may be detected by the state detection unit. In this figure, a deviation A between the further intermediate state Z3.M and the initial state Z1,M through the movement in act t6) may be minimized.

The schematic diagrams contained in the figures described do not depict any scale or size ratio.

The method described in detail above, as well as the facilities shown, merely involve exemplary embodiments, which may be modified by the person skilled in the art in a variety of ways without departing from the area of the invention. Further, the use of the indefinite article "a" or "an" does not exclude the features concerned also being present more than once. Likewise, the terms "unit" and "element" do not exclude the components concerned consisting of a number of sub-components working together, which, if necessary, may also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

What is claimed is:

1. A holder device for holding a medical instrument, the holder device comprising:

a first receiving element;

a second receiving element; and plurality of diaphragm elements within a diaphragm layer between the first receiving element and the second receiving element, the plurality of diaphragm elements being arranged about a common axis of rotation of the first receiving element and the second receiving element, wherein the common axis of rotation is substantially perpendicular to the diaphragm layer, at least a first diaphram element of the plurality of diaphgram elements includes at least one first coupling element, at least the first receiving element includes at least one second coupling element to engage with the at least one first coupling element to couple the first receiving element to at least the first diaphram, and at least the first diaphragm element is actuated by a mechanical coupling between the at least one first coupling element and the at least one second coupling element.

2. The holder device of claim 1, wherein the first coupling element is an elongated guide configured to engage with the second coupling element.

3. The holder device of claim 1, wherein the second coupling element is an elongated guide configured to engage with the first coupling element.

4. The holder device of claim 1, wherein the plurality of diaphragm elements at least partly overlap with each other.

5. The holder device of claim 1, wherein one of the first coupling element or the second coupling element is configured as a raise area, and another of the first coupling element or the second coupling element is configured as a cutout.

6. The holder device of claim 1, wherein each of the plurality of diaphragm elements has a same shape about the common axis of rotation.

7. The holder device of claim 1, wherein the plurality of diaphragm elements have a triangular, circle, or triangular and circle segment shape.

8. The holder device of claim 1, wherein the first receiving element has an opening to receive the medical instrument, the opening being a hole or a slot.

9. The holder device of claim 1, wherein at least one of the first receiving element or the second receiving element has a circular or wheel shape.

10. The holder device of claim 9, wherein the at least one of the first receiving element or the second receiving element is configured as a toothed wheel or a pulley wheel.

11. The holder device of claim 9, further comprising:

a motorized drive device configured to move the first receiving element relative to the second receiving element about the common axis of rotation.

12. The holder device of claim 1, further comprising at least one of:

a fixing device configured to lock the first receiving element in place relative to the second receiving element, or a diaphragm fixing device configured to lock the plurality of diaphragm elements in place.

13. The holder device of claim 1, wherein the first receiving element includes a plurality of second coupling elements, each of the plurality of second coupling elements corresponding to a diaphragm element, among the plurality of diaphragm elements, and each second coupling element being an elongated guide, the second receiving element includes a plurality of third coupling elements, each of the plurality of third coupling elements corresponding to a diaphragm element among the plurality of diaphragm elements, and each third coupling element being an elongated guide, at least one of the first receiving element or the second receiving element is configured as a toothed wheel, the first receiving element and the second receiving element each of have an opening to receive the medical instrument, each respective diaphragm element among the plurality of diaphragm elements has a respective first coupling element on a side of the respective diaphram element facing the first receiving element, and a respective first coupling element on a side of the respective diaphram element facing the second receiving element, and each respective first coupling element is configured as pin-shaped raised area.

14. A medical instrument holding device, comprising:

a first receiving plate;

a second receiving plate; and a diaphragm layer between the first receiving plate and the second receiving plate, the diaphragm layer including a plurality of diaphragm elements arranged about a common axis of rotation of the first receiving plate and the second receiving plate, wherein the plurality of diaphragm elements are mechanically coupled to at least the first receiving plate, and at least the first receiving plate is configured to rotate about the common axis of rotation to cause the plurality of diaphragm elements to enclose and hold a medical instrument along the common axis of rotation.

15. The medical instrument holding device of claim 14, wherein each of the first receiving plate and the second receiving plate have an opening to receive the medical instrument, a center of the opening is aligned with the common axis of rotation, and the plurality of diaphragm elements are configured to enclose and hold the medical instrument in the opening.

16. The medical instrument holding device of claim 14, wherein the plurality of diaphragm elements include a plurality of first coupling elements on a side facing the first receiving plate, the first receiving plate includes a plurality of second coupling elements, and the plurality of first coupling elements are configured to engage the plurality of second coupling elements to mechanically couple the first receiving plate to the plurality of diaphragm elements.

17. The medical instrument holding device of claim 16, wherein the plurality of diaphragm elements include a plurality of third coupling elements on a side facing the second receiving plate, the second receiving plate includes a plurality of fourth coupling elements, and the plurality of third coupling elements are configured to engage the plurality of fourth coupling elements to mechanically couple the second receiving plate to the plurality of diaphragm elements.

18. The medical instrument holding device of claim 16, wherein the plurality of first coupling elements are raised areas, the plurality of second coupling elements are elongated guides, and the plurality of first coupling elements are configured to move within the plurality of second coupling elements when engaged with the plurality of second coupling elements.

19. The medical instrument holding device of claim 14, wherein the plurality of diaphragm elements at least partly overlap with each other.

20. The medical instrument holding device of claim 14, wherein the plurality of diaphragm elements include at least three diaphragm elements.

* * * * *